United States Patent
Tas et al.

(10) Patent No.: US 7,629,352 B2
(45) Date of Patent: Dec. 8, 2009

(54) PHARMACEUTICAL COMPOSITION COMPRISING A CORTICOSTEROID AND A SPECIFIC INHIBITOR OF HEDGEHOG/SMOOTHENED SIGNALING

(75) Inventors: Sinan Tas, S. Hasan Tuncel Caddesi No. 36, Bor (TR) 51700; Oktay Avci, Izmir (TR)

(73) Assignee: Sinan Tas, Bor (TR)

( * ) Notice: Subject to any disclaimer, the term of this patent is extended or adjusted under 35 U.S.C. 154(b) by 0 days.

(21) Appl. No.: 11/874,653

(22) Filed: Oct. 18, 2007

(65) Prior Publication Data

US 2008/0090790 A1    Apr. 17, 2008

Related U.S. Application Data

(60) Division of application No. 10/682,662, filed on Oct. 9, 2003, which is a continuation-in-part of application No. PCT/TR02/00017, filed on Apr. 19, 2002, and a continuation-in-part of application No. PCT/TR01/00027, filed on Jul. 2, 2001.

(51) Int. Cl.
    A61K 31/438    (2006.01)
(52) U.S. Cl. .................................................... 514/278
(58) Field of Classification Search ................. 514/278
    See application file for complete search history.

(56) References Cited

U.S. PATENT DOCUMENTS

| 4,370,322 | A | 1/1983 | Busse et al. | |
|---|---|---|---|---|
| 6,291,516 | B1 | 9/2001 | Dudek et al. | |
| 6,432,970 | B2 | 8/2002 | Beachy et al. | |
| 6,951,839 | B1 | 10/2005 | Crompton | |
| 2002/0165221 | A1 | 11/2002 | Baxter et al. | |
| 2003/0119786 | A1* | 6/2003 | Keith et al. | 514/81 |
| 2004/0072914 | A1 | 4/2004 | Tas et al. | |

FOREIGN PATENT DOCUMENTS

| CA | 2416731 | 1/2003 |
|---|---|---|
| WO | 9835020 | 8/1998 |
| WO | 9952534 | 10/1999 |
| WO | 0041545 | 7/2000 |
| WO | 0074706 | 12/2000 |
| WO | 0127135 A2 | 4/2001 |
| WO | 0140438 A2 | 6/2001 |
| WO | 0198344 | 12/2001 |
| WO | 0207702 | 1/2002 |
| WO | 0230462 | 4/2002 |
| WO | 02078703 | 10/2002 |
| WO | 02080952 | 10/2002 |

OTHER PUBLICATIONS van der Vleuten et al. Arch. Dermatol. Res., 1999, vol. 291, pp. 390-395.*

Nilsson M et al, "Induction of Basal Cell Carcinomas and Trichoephitheliomas in Mice Overexpressing GLI-1", Proc. Nat'l Acad. Sci. USA 2000; 97:3438-3443.

Suzuki, Hidekazu et al, "Down regulation of a morphogene(sonic hedgehog) gradient in the gastric epithelium of *Helicobacter pylori*-infected Mongolian gerbils", J. Pathol 2005: 206:187-197.

Sheng, Tao et al, "Activation of the hedgehog pathway in advanced prostate cancer", Molecular Cancer 2004, 3:29.

Kumamoto, Hiroyuki et al, "Expression of Sonic Hedgehog (SHH) signaling molecules in ameloblastomas", J. Oral Pathol Med (2004) 33: 185-190.

Xuan, Yan Hua et al, "Enhanced expression of hedgehog signaling molecules in squamous cell carcinoma of uterine cervix and it precursor lesions", Modern Pathology (2006) 19, 1139-1147.

Hannun, Yusuf A., Blood: Apoptosis and the Dilemma of Cancer Chemotherapy, The Journal of The American Society of Hematology, vol. 89, No. 6, Mar. 15, 1997, pp. 1845-1853.

Bijlsma, Maarten F., et al :Repression of Smoothened by Patched-Dependetn (Pro-) Vitamin D3 Secrettion, PloS Biology, Aug. 2006, vol. 4, Issue 8, pp. 1397-1410.

Dahmane, N. et al, "Activation of the Trnascription of factor Gli1 and the Sonic hedgehog signalling pathway in skin tumours", Nature, vol. 389, Oct. 23, 1997, pp. 876-881.

Wicking, Carol et al "The Hedgehog Signalling Pathway in Tumorigenesis and Development", Oncogene (1999), vol. 18, pp. 7844-7851.

Hahn, Heidi et al, "The Patched Signaling Pathway in Tumorigeneis and Development: Lessons from Animal Models". J. Mol. Med (1999) vol. 77, pp. 459-468.

Kutney, James P. et al "Synthetic Studies in the veratrum Alkaloid Series II. The Total Synthesis of Verarine, Veratramine, Jervine and Veratrobasine", Can. J. Chem. vol. 53, 1975, pp. 1796-1817.

Krauss. S., et al "A functionally conserved homolog of the drosophila segment polarity gene hh is expressed in tissues with polarizing activity in zebrafish embryos",Cell vol. 75. pp. 1431-1444. Dec. 31, 1993.

Bellom, F. et al "Identification of Sonic hedgehog as a candidate gene responsible for holoprosencephaly", Nature Genetics vol. 14, Nov. 1996, pp. 353-356.

(Continued)

*Primary Examiner*—Ardin Marschel
*Assistant Examiner*—James D Anderson

(57) ABSTRACT

This invention concerns the use of cyclopamine, a naturally occurring steroidal alkaloid known for over thirty years, for the treatment of psoriasis and achievement of rapid clearance of the psoriatic skin lesions together with the reversion of the histopathological signs of disease to normalcy with no detectable side effects. The cyclopamine-induced clearance of psoriatic lesions from the skin of patients is associated with the causation of cellular differentiation in lesional epidermis and with the rapid disappearance of CD4(+) lymphocytes and other inflammatory cells from lesional skin. Therapeutic compositions comprising of cyclopamine and a corticosteroid and/or the pre-treatment of lesions with a corticosteroid provide significantly further increased therapeutic effectiveness over the use of cyclopamine alone or a corticosteroid alone.

9 Claims, 8 Drawing Sheets

OTHER PUBLICATIONS

Roessler, Erich et al, "Mutations in the human Sonic Hedge hog gene cause holoprosencephaly", Nature Genetics, vol. 14, Nov. 1996, pp. 357-360.

Chiang, Chin, et al "Cyclopia and defective axial patterning in mice lacking Sonic Hedgehog gene function", Nature, vol. 383, Oct. 3, 1996, pp. 407-413.

Ericson, Johan et al "Two critical periods of sonic hedgehog signaling required for the specifciation of motor neuron identity", Cell. vol. 87, pp. 661-673, Nov. 15, 1996.

Chuang, Pao-Tien et al "Vertebrate hedgehog signalling modulated by induction of a hedgehog-binding protein" Nature vol. 397, Feb. 18, 1999, pp. 617-621.

Wang, Li Chun et al, "Conditional Disruption of Hedgehog Signaling Pathway Defines its Critical Role in Hair Development and Regeneration", The Journal of Investigative Dermatology, vol. 114, No. 5, May 2000, pp. 901-908.

Williams, Kevin P. et al "Functional antagonists of sonic hedgehog reveal the importance of the N terminus for activity". Journal of Cell Structure, vol. 112, (1999) pp. 4405-4414.

Bovenschen, H. J., et al, "Explorative immunohistochemical study of the evaluate the additional of a topical corticosteriod in the early phase of alefacept treatment for psoriasis", Arc Dermatol Res. (2007), 298: 457-463.

Gniadecki, Robert, "Effects of 1,25-dihydroxyvitamin D3 and its 20-epi analogues (MC 1288, MC 1301, KH 1060), on clonal keratinocyte growth: evidence for differentiation of keratinocyte stem cells and analysis of the modulatory effects of cytokines". Britsh Journal of Pharmacology (1997) vol. 120, pp. 1119-1127.

Oro, Anthony E., et al "Basel Cell Carcinomas in Mice Overexpressing Sonic Hedgehog", Science, vol. 276, May 2, 1997, pp. 817-821.

Hopyan Seva et al "Indian Hedgehog and Parathyroid hormone related protein signaling in cartilage tumors of bone." Proceedings Of the American Association For Cancer Research Annual, No. 41, Mar. 2000 p. 206 XP008001019, 91st Annual Meeting of the American Association for Cancer Research, San Francisco, CA, US, April Jan. 05, 2000, Mar. 2000, ISSN< 0197-016X Abstract.

Chen et al "Analysis of the zebrafish smoothened mutant reveals conserved and divergent functions of hedgehog activity", Development 128, 2385-2396 (2001).

Vorechovsky, Igor et al, "Trichoepitheliomas Contain Somatic Mutations in the Overexpressed PTCH Gene: Support for a Gatekeeper Mechanism in Skin Tumorigenesis", Cancer Research 57, 4677-4681, Nov. 1, 1971.

Keeler, Richard F., "Teratogenic Effects of Cyclopamine and Jervine in Rats, Mice and Hamsters," Proceedings of the Society for Experimantal Biology and Medicine, vol. 149, pp. 302-306 (1975) Copyright © 1975 by the Society for Experimental Biology and Medicine.

Maesawa, Chihaya et al, "Mutations in the Human Homologue of the Drosophila Patched Gene in *Esophageal Squamous* Cell Carsinoma", Genes, Chromosones & Cancer 21:276-279, (1998).

Omnell, M.L. et al., "Expression of Veratrum Alkaloid Teratogenicity in the Mouse," Teratology, vol. 105-119 (1990).

Talpale Jussi et al., "Effects of oncogenic mutations in Smoothened and Patched can be reversed by cyclopamine," Nature, vol. 406, pp. 1005-1009 (Aug. 31, 2000) © 2000 Macmillan Magazines Ltd.

Xie, Jingwa et al, "Mutations of the Patched Gene in Several Types of SPoradic Extracutaneous Tumors", Cancer Research 57, pp. 2369-2372, Jun. 15, 1997.

Michimukai, Eiji et al., "Mutations in the Human Homologue of the *Drosophila* Segment Polarity Gene Patched in Oral Squamous Cell Carcinoma Cell Lines," in Vitro Cellular & Developmental Biology, vol. 37, No. 7, pp. 459-464 (Jul./Aug. 2001) ProQuest Medical Library.

Berman, David M. et al., "Medulloblastoma Growth Inhibition by Hedgehog Pathway Blockade," Science, vol. 297, pp. 1559-1561 (Aug. 30, 2002).

Watkins, D. Neil et al., "Hedgehog signaling within airway epithelial progenitors and in small-cell lung cancer," Nature, vol. 422, pp. 313-317 (Mar. 20, 2003) © 2003 Nature Publishing Group.

Thayer, Sarah P. et al., "Hedgehog is an early and late mediator of pancreatic cancer tumorigenesis," Nature, vol. 425, pp. 851-856 (Oct. 23, 2003).

Qualtrough, David et al., "Hedgehog Signalling in Colorectal Tumour Cells: Induction of Apoptosis with Cyclopamine Treatment," Int. J. Cancer, vol. 110, pp. 831-837 (2004) © 2004 Wiley-Liss, Inc.

Struhl, Gary et al, "Hedgehog organises the pattern and polarity of epidermal cells in the Drosophila abdomen", Development 124, 2143-2154 (1997).

Kimonis, V. E., "Clinical Manifestations in 105 Persons with Nevoid Basal Cell Carcinoma Syndrome", American Journal of Medical Genetics 69:299-308 (1997).

Goodman & Gilman's, The Pharmacological Basis of Therapeutics, Ninth Edition, (1996), Calabresi et al., Section X, Chemotherapy of Neoplastic Diseases, pp. 1225-1229.

Tas S et al, Induction of the differentiation and apoptosis of tumor cells in vivo with efficiency and selectivity. European Journal of Dermatology 2004; 14:96-102.

Riddle RD et al, Sonic hedgehog Mediates Polarizing Activity of the ZPA. Cell 1993; 75:1401-1416.

Basler K et al, Compartment boundaries and the control of Drosophila limb pattern by hedgehog protein. Nature 1994; 368: 208-214.

Kojima T et al, Induction of a mirror-image duplication of anterior wing structures by localized hedgehog expression in the anterior compartment of Drosophila melanogaster wing imaginal discs. Gene 1994; 148:211-217.

Heberlein U et al, Growth and differentiation in the Drosophila eye coordinated by hedgehog. Nature 1995; 373: 709-711.

Lepage T et al, "Signal transduction by cAMP-dependent protein kinase A in Drosophila limb patterning". Nature 1995; 373: 711-715.

Sanchez, Pilar et al, "In Vivo Inhibition of Endogenous Brain Tumors Through Systemic Interference of Hedgehog signaling in Mice", Mechanisms of Development, 122 (2005) pp. 223-230.

Bellusci S et al, "Involvement of Sonic hedgehog (Shh) in mouse embryonic lung growth and morphogenesis". Development 1997; 134: 53-63.

Litingtung Y et al, "Sonic hedgehog is essential to foregut development. Nature Genetics 1998; 20: 58-61."

Orentas DM et al, "Sonic hedgehog signaling is required during the appearance of spinal cord oligodendrocyte precursors". Development 1999; 126:2419-2429.

Furumichi T et al, "Adenosine 3':5'-cyclic monophosphate inhibits in vitro angiogenesis induced by endothelial cell growth factor". Japanese Heart Journal 1992; 33: 373-382.

Tsopanoglou NE et al, "Opposing effects on modulation of angiogenesis by protein kinase C and cAMP-mediated pathways". Journal of Vascular Research 1994; 31: 195-204.

Johnson RL et al, "Patched overexpression alters wing disc size and pattern: transcriptional and post-transcriptional effects on hedgehog targets". Development 1995; 121: 4161-4170.

deCelis JF et al, "Ventral veinless, the gene encoding the Cf1a transcription factor, links positional information and cell differentiation during embryonic and imaginal development in *Drosophila melanogaster*". Development 1995; 121: 3405-3416.

Roberts D. J. et al, "Sonic hedgehog is an endodermal signal inducing Bmp-4 and Hox genes during induction and regionalization of the chick hindgut". Development 1995; 121: 3163-3174.

Winnier G et al, "Bone morphogenetic protein-4 is required for mesoderm formation and patterning in the mouse". Genes & Development 1995; 9: 2105-2116.

Bavik C et al, Developmental abnormalities in cultured mouse embryos deprived of retinoic acid by inhibition of yolk sac retinol binding protein synthesis. Proceedings of the National Academy of the Sciences o f USA 1996; 93: 3110-3114.

Dickson MC et al, Defective haematopoiesis and vasculogenesis in transforming growth factor-beta 1 knock out mice. Development 1995; 121: 1845-1854.

D'Angelo G et al, cAMP-dependent protein kinase inhibits the mitogenic action of vascular endothelial growth factor and fibroblast growth factor in capillary endothelial cells by blocking Raf activation. Journal of Cell Biochemistry 1997; 6767: 353-366.

Farrington SM et al, Winged-Helix, Hedgehog and Bmp genes are differentially expressed in distinct cell layers of the murine yolk sac. Mechanisms of Development 1997; 62: 197-211.

St Amand TR et al, Cloning and expression pattern of chicken Pitx2: A new component in the Shh signaling pathway controlling embryonic heart looping. Biochemical and Biophysical Research Communications 1998; 247: 100-105.

Pepicelli CV et al, Sonic hedgehog regulates branching morphogenesis in the mammalian lung. Current Biology 1998; 8: 1083-1086.

Grabel L et al, Using EC and ES cell culture to study early development: recent observations on Indian hedgehog and Bmps. International Journal of Developmental Biology 1998; 42: 917-925.

St Jacques B et al, Indian hedgehog signaling regulates proliferation and differentiation of chondrocytes and is essential for bone formation. Genes & Development 1999; 13: 2072-2086.

Brown LA et al, Insights into early vasculogenesis revealed by expression of the ETS-domain transcription factor Fli-1 in wild type and mutant zebrafish embryos. Mechanisms of Development 2000, 90: 237-252.

Maye P. et al, Indian hedgehog signaling in extraembryonic endoderm and ectoderm differentiation in ES embryoid bodies. Mechanisms of Development 2000; 94: 117-132.

Dyer M et al, Indian hedgehog activities hematopoiesis and vasculogenesis and can respecify prospective neuroectodermal cell fate in the mouse embryo. Development 2001; 128: 1717-1730.

Braybrooke JP et al, A phase II study of razoxane, an antiangiogenic topoisomerase II inhibitor, in renal cell cancer with assessment of potential surrogate markers of angiogenesis. Clinical Cancer Research 2000; 6: 4697-4704.

Dunn MK et al, Cyclopamine, A Steroidal Alkaloid Disrupts Development of Neural Crest Cells in Xenopus. Developmental Dynamics 1995; 202: 255-270.

Tas S et al, Rapid clearance of psoriatic skin lesions induced by topical cyclopamine. Dermatology 2004; 209: 126-131.

Sauder et al, Neovastat (AE-941), an inhibitor of angiogenesis: Randomized phase I/II clinical trial results in patients with plaque psoriasis. J Am Acad Dermatol; vol. 47, No. 4, 2002; 535-541.

Mimeault, Murielle, et al "Cytotoxic effects induced by a combination of cyclopamine and gefitinib, the selective hedgehog and epidermal growth factor receptor signaling in hibitors in prostate cancer cells", Int. J. Cancer: 118, 1022-1031 (2006).

Lebwohl Mark et al , "A randomized, double blind, placebo controlled study of clabetasol propionate 0.05% foam in the treatment of nonscalp psoriasis", International Journal of Dermatology, 2002, vol. 41, pp. 269-274.

"The Merk Manual of Diagnosis and Therapy" Merck Research Laboratories, 1999, p. 817.

Mohler J. et al "Activation of Knot (kn) Specifies the 3-4 Intervein Region in the Drosophila Wing". Development 2000:127:55-63.

Al-Suwaidan, S. N. et al., "Clearance is not a realistic expectation of psoriasis treatment", J Am Acad Dermatol, vol. 42, No. 5, Part 1, May 2000, pp. 796-802.

Ashcroft, D.M. et al., "Therapeutic strategies for psoriasis", Journal of Clinical Pharmacy and Therapeutics, 25, 2000, pp. 1-10.

Berman David M et al., Inhibition of prostate morphogensis by the Sonic hedgehog pathway inhibitor cyclopamine. The Journal of Urology, vol. 163, No. 4 Suppl., Apr. 2000, p. 204 XP008001018, 95th Annual Meeting of the American Urological Association, Inc.; Atlanta, Georgia, USA; Apr. 29, 2000-May 4, 1999 abstract.

Binns W. et al., "Congenital Cyclopian-Type Malformation in Lambs Induced by Maternal Ingestion of a Rage Plat, *Veratrum californicum*", A.M. J. Vet. Res., Nov. 1963, 24, 103, pp. 1164-1175.

Bowman P.H. et al., "Combination of calcipotriene (Dovonex) ointment and tazarotene (Tazorac) gel versus clobetasol ointment in the treatment of plaque psoriasis: A pilot study", J. Am. Acad Dermatol, vol. 46, No. 6, Jun. 2002, pp. 907-913.

Cooper M.K. et al., "Teratogen-Mediated Inhibition of Target Tissue Response to Shh Signaling", Science, vol. 280, Jun. 5, 1998, pp. 1603-1607.

Detmer K. et al., "Erythroid differentiation in vitro is blocked by cyclopamine, an inhibitor of hedgehog signaling." Developmental Biology, vol. 222 No. 1, Jun. 1, 2000, p. 242 XP008001023, Fifty-ninth Annual Meeting of the Society for Development Biology; Boulder, Colorado, USA; Jun. 7-11, 2000, ISSN: 0012-1606 abstract.

Elder J.T. et al., "The Genetics of Psoriasis 2001 The Odyssey Continues", Arch Dermatol, vol. 137, Nov. 2001, pp. 1447-1454.

Goodrich L.V et al., "Hedgehog and Patched in Neural Development and Disease", Neuron, vol. 21, Dec. 1998, pp. 1243-1257.

Gottlieb S. L. et al., "Response of psoriasis to a lymphocyte-selective toxin (DAB398OL-2) suggest a primary immune, but not keratinocyte, pathogenic basis", Nature Medicine, vol. 1, No. 5, May 1995, pp. 442-447.

Incardona JP et al., "The teratogenic Veratrum alkaloid cyclopamine inhibits Sonic hedgehog signal transduction", Development 125, (1998), pp. 3553-3562.

Kanitakis J. et al., "Expression of the hair stem cell-specific keratin 15 in pilar tumors of the skin", European Journal of Dermatology, 1999, 9, pp. 363-365.

Keeler R.F. "Teratogenic Compounds of *Veratrum californicum* (Durand)—Vi", Phytochemistry, vol. 8, (1969) pp. 223-225.

King L.E. et al., "Epidermal Growth Factor/Transforming Growth Factor Alpha Receptors and Psoriasis", The Society for Investigative Dermatology, Inc., vol. 95, No. 5, Supplement, Nov. 1990, pp. 105-125.

Kooy AJ et al., Expression of E-Cadherin, a—& B—Catenin and CD44V6 and the Subcellular Localization of E-Cadherin and CD44V6 in Normal Epidermis and Basal Cell Carcinoma, Human Pathology, vol. 30, No. 11, Nov. 1999, pp. 1328-1335.

Krueger J.G., "The immunologic basis for the treatment of psoriasis with new biologic agents", J Am Acad Dematol, vol. 46, No. 1, Jan. 2002, pp. 1-23.

Lebwohl M. et al., "Treatment of psoriasis. Part 1. Topical therapy and phototherapy", J Am Acad Dermatol, vol. 45, No. 4, Oct. 2001, pp. 487-498.

Bollag, Wendy B., et al, "8-CL-Adenosine enahnces 1, 25-dihydroxyvitamin D3—induced growth inhibition without affecting 1, 25-dihydroxyvitamin D3—stimulated differentiation of primary mouse epidermal keratinocytes",BMC Pharmacology, 2004, 4:13.

Lyle S. et al., "The C8/144B monoclonal antibody recognizes cytokeratin 15 and defines the location of human hair follicle stem cells", Journal of Cell Science, 111, 1998, pp. 3179-3188.

Nickoloff B. J., "The Immunologic and Genetic Basis of Psoriasis", Arch Dermatol, vol. 135, Sep. 1999, pp. 1104-1110.

Outram S. V. et al., "Hedgehog Signaling Reglates Differentiation from Doble-Negative to Double-Positive Thymocyte", Immunity, vol. 13, Aug. 2000, pp. 187-197.

Spuls P. I. et al., "A systematic review of five systemic treatments for severe psoriasis", British Journal of Dermatology, 137, 1997, pp. 943-949.

Zhang Y. et al., "Hedgehog acts as a somatic stem cell factor in the Drosophila ovary", Nature, vol. 410, Mar. 29, 2001, pp. 599-604.

Levine, Edward M. et al., Sonic Hedgehog Promotes Rod Photoreceptor Differentiation in Mammalian Retinal Cells In Vitro, The Journal of Neuroscience, Aug. 15, 1997, 17(16):6277-6288.

Kim, Seung K. et al., "Pancreas development is promoted by cyclopamine, a Hedgehog signaling inhibitor," Proc. Natl. Acad. Sci. USA, vol. 95, pp. 13036-13041, Oct. 1998, Developmental Biology.

James P. Kutney et al, Synthesis Studies in the Veratrum Alkaloid Series, II. The Total Synthesis of Verarine, Veratramine, Jervine and Veratrobasine, Canadian J. Chemical, vol. 53, 1975, pp. 1796-1817.

Lu, X. et al "Loss of heterozygosity among tumor suppressor genes in invasive and in situ carcinoma of the uterine cervix", Int. J. Gynecol Cancer 2000, 10, pp. 452-458.

Fisher, Daniel et al, "Vertebrate HoxB gene expression requires DNA replication", European Molecular Biology Organization Journal, vol. 22, No. 14, pp. 373-3748, 2003.

Stenkamp, Deborah L., "Function for Hedgehog Genes in Zebrafish Retinal Development," Developmental Biology, vol. 220, pp. 238-252 (2000).

Treier, Mathias et al., "Hedgehog signaling is required for pituitary gland development," Development 128, pp. 377-386 (2001), Printed in Great Britain © The Company of Biologists Limited 2001.

Kahane, Nitza et al., "The third wave of myotome colonization by mitotically competent progenitors: regulating the balance between differentiation and proliferation during muscle development," Development 128, pp. 2187-2198 (2001), Printed in Great Britain © The Company of Biologists Limited 2001.

Fan, Hongran et al., "Sonic Hedgehog Opposes Epithelial Cell Cycle Arrest," The Journal of Cell Biology, vol. 147, No. 1, Oct. 4, 1999, pp. 71-76.

Sukegawa, Akiko et al., "The concentric structure of the developing gut is regulated by Sonic hedgehog derived from endodermal epithelium," Development 127, pp. 1971-1890 (2000), Printed in Great Britain © The Company of Biologists Limited 2000.

Zhang, Jian et al., "Downregulation of Hedgehog Signaling Is Required for Organogenesis of the Small Intestine in Xenopus," Developmental Biology, vol. 229, pp. 188-202 (2001).

Van Den Brink, Gus R. et al., "Sonic Hedgehog Regulates Gastric Gland Morphogenesis in Man and Mouse," Gastroenterology, vol. 121, pp. 317-328 (2001).

Ramalho-Santos, Miguel et al., "Hedgehog signals regulate multiple aspects of gastrointestinal development," Development 127, pp. 2763-2772 (2000), Printed in Great Britain © The Company of Biologists Limited 2000.

Ishizuya-Oka, Atsuko et al., "Thyroid hormone-induced expression of Sonic hedgehog correlates with adult epithelial development during remodeling of the Xenopus stomach and intestine," Differentiation, vol. 69, pp. 27-37 (2001).

van den Brink, G.R. et al., "Sonic hedgehog expression correlates with fundic gland differentiation in the adult gastrointestinal tract," Gut, vol. 51, pp. 628-633 (2002).

Perron, Muriel et al., "A novel function for Hedgehog signaling in retinal pigment epithelium differentiation," Development 130, vol. 130, pp. 1565-1577, © 2003 The Company of Biologists Ltd.

Watkins, D. Neil et al., "Hedgehog signaling within airway epithelial progenitors and in small-cell lung cancer," Nature, vol. 422, pp. 313-317 (Mar. 20, 2003) © 2003 Nature Publishing Group.

Stenkamp, Deborah L., "Extraretinal and retinal hedgehog signaling sequentially regulate retinal differentiation in zebrafish," Departmental Biology, vol. 258, pp. 349-363 (2003) © 2003 Elsevier Science (USA).

Niemann, C. et al., "Indian hedgehog and β-catenin signaling: Role in the sebaceous lineage of normal and neoplastic mammalian epidermis," PNAS, vol. 100, Supplement 1, pp. 11873-11880 (Sep. 30, 2003).

Jarov, Artem et al., "A dual role for Sonic hedgehog in regulating adhesion and differentiation of neuroepithelial cells," Developmental Biology, vol. 261, pp. 520-536 (2003) © 2003 Elsevier Inc.

Allen, Mary et al., "Hedgehog Signaling Regulates Sebaceous Gland Development," American Journal of Pathology, vol. 163, No. 6, pp. 2173-2178 (Dec. 6, 2003) Copyright © American Society for Investigative Pathology.

Yao, Humphrey Hung-Chang et al., "Desert Hedgehog/Patched 1 signaling specifies fetal Leydig cell fate in testis organogenesis," Genes & Development, vol. 16, pp. 1433-1440 © 2002 by Cold Spring Harbor Laboratory Press.

Wang, Bu-er et al., "Inhibition of Epithelial Ductal Branching in the Prostate by Sonic Hedgehog Is Indirectly Mediated by Stromal Cells," The Journal of Biological Chemistry, vol. 278, No. 20, pp. 18506-18513 (May 16, 2003) © 2003 by the American Society for Biochemistry and Molecular Biology, Inc.

Freestone, Sarah H. et al., "Sonic hedgehog regulates prostatic growth and epithelial differentiation," Developmental Biology, vol. 264, pp. 352-362 (2003).

Berman, David M. et al. "Widespread requirement for Hedgehog ligand stimulation in growth of digestive tract tumours," Nature, vol. 425, pp. 846-851 (Oct. 23, 2003).

Grachtchouk, Vladimir et al., "The magnitude of hedgehog signaling activity defines skin tumor phenotype," The EMBO Journal, vol. 22, No. 11, pp. 2741-2751 (2003).

Zhang, Yan et al., "Hedgehog acts as a somatic stem cell factor in the Drosophila ovary," Nature, vol. 410, pp. 599-604 (Mar. 29, 2001) © 2001 Macmillan Magazines Ltd.

Stone, Donna M. et al, "The tumour-suppressor gene patched encodes a candidate receptor for Sonic hedgehog", Nature. vol. 384. Nov. 14, 1996. pp. 129-134.

Oliver, Trudy G., et al "Loss of patched and disruption of granule cell development in a pre-neoplastic stage of medulloblastoma" Development and Disease 132. 2005. pp. 2425-2439.

Williamham, Mark C., "Cytochemical Methods for the Detection of Apoptosis", The Hisochemical Society, Inc., vol. 47 (9), pp. 1101-1109. The Journal of Histochemistry and Cytochemistry. vol. 47(9): 1101-1109, 1999.

Celso et al.,"Transient activation of B-catenin signaling in adult mouse epidermis is sufficient to induce new hair follicles but continuous activation is required to maintain hair follicle tumours," Development 131, 1787-1799. 2004.

Stenkamp DL et al. "Function for Hedgehog Genes in Zebrafish Retinal Development," Developmental Biology 220, 238-252 (2000).

Stenkamp DL et al. "Extraretinal and retinal hedgehog signaling sequentially regulate retinal differentiation in zebrafish," Devolpmental Biology 258, (2003) 349-363.

Atienza JM et al. "Identification of Inhibitor Specificity Determinants in a Mammalian Phosphodiesterase," The Journal of Biological Chemistry, (1999), 4839-4847.

Broadbear JH et al. "Methocinnamox Is a Potent, Long-Lasting, and Selective Antagonist of Morphine-Mediated Antinociception in the Mouse: Comparison with Clocinnamox, B-Funaltrexamine, and B-Chlornaltrexamine" The Journal of Phamacology and Experimental Therapeutics, (2000), 933-940.

Ciardiello F et al. "Interactions between the Epidermal Growth Factor Receptor and Type I Protein Kinase A: Biological Significance and Therapeutic Implications" Clinical Cancer Research (1998), 821-828.

Hata A et al. "Smad6 inhibits BMP/Smad1 signaling by specifically competing with the Smad4 tumor suppressor" Genes and Development, (1998) 186-197.

Hoffmeyer A et al. "Different Mitogen-activated Protein Kinase Signaling Pathways Cooperate to Regulate Tumor Necrosis Factor Gene Expression in T Lymphocytes" The Journal of Biological Chemistry, (1999), 4319-4327.

Humphries RG et al. "FPL 66096: a novel, highly potent and selective antagonist at human platelet P2t-purinoceptors" Br. J. Pharmacol. (1994) 113, 1057-1063.

Liu Y. et al. "Structural basis for selective inhibition of Src family kinases by PP1" Chemistry & Biology (1999) 671-678.

Manthey CL et al. "SB202190, a selective inhibitor of p38 mitogen-activated protein kinase, is a powerful regulator of LPS-induced mRNAs in monocytes" Journal of Leukocyte Biology (1998) 409-417.

Read M. et al. "Structure-based design of selective and potent G quadruplex-mediated telomerase inhibitors" PNAS, Apr. 24, 2001, vol. 98, No. 9, pp. 4844-4849.

Yu TK et al. "IL-2 Activation of NK Cells: Involvement of MKK1/2/ERK But Not p38 Kinase Pathway" The Journal of Immunology, (2000), 6244-6251.

van der Vleuten et al. "Clobetasol-17-propionate lotion under hydrocolloid dressing (Duoderm ET) once weekly versus unoccluded clobetasol-17-propionate ointment twice daily in psoriasis: an immunohistochemical study on remission and relapse" Archives of Dermatological Research. 1999;291:390-395.

Methot N. et al. "An absolute requirement for Cubitus interruptus in Hedgehog signaling" Development 2001;128:733-742.

Diehl AJ et al. "Glycogen synthase kinase-3b regulates cyclin D1 proteolysis and subcellular localization" Genes & Delvelopment 1998;12:3499-3511.

Nasevicius A et al. "Effective targeted gene 'knockdown' in zebrafish" Nature Genetics 2000;26:216-220.

Treier M et al. "Hedgehog signaling is required for pituitary gland development" Development 2001;128:377-386.

Coventry S et al. "Cyclopamine-Induced Holoprosencephaly and Associated Craniofacial Malformations in the Golden Hamster: Anatomic and Molecular Events" Pediatric and Developmental Pathology 1998;1:29-41.

Motzny CK et al. "The Drosophila cubitus interruptus protein and its role in the wingless and hedgehog signal transduction pathways" Mechanisms of Development 1995;52:137-150.

Katsuura M et al. "The NH2-terminal region of the active domain of sonic hedgehog is necessary for its signal transduction" FEBS Letters 447 (1999) 447:325-328.

Mastronardi, FG et al. "Attenuation of Experimental Autoimmune Encephalomyelitis and Nonimmune Demyelination by IFN-B plus Vitamin B12: Treatment to Modify Notch-1/Sonic Hedgehog Balance" The Journal of Immunology (2004) 172:6418-6426.

Akazawa C et al. "The Unregulated Expression of Sonic Hedgehog in Motor Neurons after Rat Facial Nerve Axotomy" Journal of Neuroscience 2004;24:7923-7930.

* cited by examiner

PHARMACEUTICAL COMPOSITION COMPRISING A CORTICOSTEROID AND A SPECIFIC INHIBITOR OF HEDGEHOG/SMOOTHENED SIGNALING

CROSS REFERENCE

This application is a division of U.S. application Ser. No. 10/682,662, filed 9 Oct. 2003 which is a continuation-in-part of PCT/TR02/00017, filed 19 Apr. 2002 designating the United States, and a continuation-in-part of PCT/TR01/00027, filed 2 Jul. 2001 designating the U.S. U.S. application Ser. No. 10/682,662, PCT/TR02/00017, and PCT/TR01/00027 are incorporated herein by reference in their entirety.

BACKGROUND OF THE INVENTION

Psoriasis is a common chronic disease affecting around 2% of the general population and any person from infancy to old age. Its etiology and pathogenesis are unclear. Family and twin studies have suggested a polygenic influence but the nature and the mechanisms of action of the involved genes are unknown (Elder J T at al. (2001) Arch. Dermatol. 137:1447-1454). Environmental factors such as streptococcal infections and trauma to the skin are also associated with the formation of psoriatic lesions. How do these environmental factors contribute to psoriasis are again unclear. However the association with streptococcal infections, immunosuppressive actions of most of the current anti-psoriatic treatments and other findings are used widely to argue for an autoimmune nature of the disease and triggering by T Lymphocytes (Gottlieb S. L. et al (1995) Nat. Med. 1:442-447; Nickoloff B. J. (1999) Arch. Dermatol. 135:1104-1110; Krueger J. G. (2002) J. Am. Acad. Dermatol. 46:1-23).

Psoriasis vulgaris, characterized by Well-demarcated scaly erythematous plaques of varying sizes anywhere on the skin, is the most common form of psoriasis. Histopathological examinations of the psoriatic skin lesions reveal typical epidermal and dermal changes that include the following.

Epidermal hyperplasia with elongation and thickening of rete ridges.

Thinning of the suprapapillary epidermis.

Focal losses or decrease of the thickness of the granular layer of epidermis.

Infiltration of the subepidermal region of dermis with neutrophils and mononuclear inflammatory cells.

Dilatation and tortuosity of the capillaries in the papillary dermis, accompanied often by papillary edema.

"Munro microabcesses", defined as focal intracorneal collections of neutrophils. Psoriatic skin lesions generally contain majority of the above listed histopathological changes and all changes can be found in a well-developed psoriatic lesion. In addition immunohistochemical and other indicators of the proliferating cells reveal presence of proliferating keratinocytes in the suprabasal layers of psoriatic lesional skin (proliferating cells are normally restricted to the basal layer of epidermis in healthy skin).

Obscurity of the etiology and pathogenesis of psoriasis has been reflected by the varied treatment strategies used for this disease (Spuls P. I. et al. (1997) Br. J. Dermatol. 137:943-949; Ashcroft D. M. et al. (2000) J. Clin. Pharm. Ther. 25:1-10; Al-Suwaidan S. N. et al. (2000) J. Am. Acad. Dermatol. 42:796-802; Lebwohl M. et al. (2001) J. Am. Acad. Dermatol. 45:487-498; Lebwohl M. et al. (2001) J. Am. Acad. Dermatol. 45:649-661). Currently common treatments include the topical corticosteroids, systemic administration of immunosuppressants (usually cyclosporine), ultraviolet irradiation of the affected skin with or without psoralen, systemic retinoids and systemic methothrexate (Spuls P. I. et al. (1997) Br. J. Dermatol. 137:943-949; Ashcroft D. M. et al. (2000) J. Clin. Pharm. Ther. 25:1-10; Lebwohl M. et al. (2001) J. Am. Acad. Dermatol. 45:487-498; Lebwohl M. et al. (2001) J. Am. Acad. Dermatol. 45:649-661). At present there is no cure for psoriasis and patients face a need for life-long treatment. Therefore relatively simpler treatments (usually topical keratolitics and corticosteroids) are considered first and when these fail, the more effective systemic treatments with more serious side effects are attempted. When the therapeutic aim is defined as the clearance of lesions, even the most effective systemic treatments are reported to fail in as many as one fourth of patients in large series (Spuls P. I. et al. (1997) Br. J. Dermatol. 137:943-949) and, because of the serious side effects, patients and physicians are advised that at present "complete clearance is not a realistic expectation" (Al-Suwaidan S. N. et al. (2000) J. Am. Acad. Dermatol. 42:796-802). In practice side effects usually limit the more potent treatments to shorter-term management [cyclosporine is nephrotoxic and strongly immunosuppressive, methotrexate is hepatotoxic, ultraviolet irradiation-psoralen is mutagenic/carcinogenic (Lebwohl M. et al. (2001) J. Am. Acad. Dermatol. 45:649-661)]. However, in the long term, topical carticosteroids are also not devoid of side effects (Lebwohl M. et al (2001) J. Am. Acad. Dermatol. 45:487-498). Currently available treatments require in general several weeks (typically 6-8 weeks) from the initiation of treatment to the appearance of objective clinical regression (Al-Suwaidan S. N. et al. (2000) J. Am. Acad. Dermatol. 42:796-802; Lebwohl M. et al. (2001) J. Am. Acad. Dermatol. 45:649-661).

Cyclopamine is a steroidal alkaloid that occurs naturally in the Veratrum plants. Teratogenicity of these plants on grazing pregnant animals led to the identification of cyclopamine as an active compound (Keeler R. F. (1969) Phytochemistry 8:223-225). How might have cyclopamine displayed teratogenicity was revealed by the finding that it is an inhibitor of the hedgehog/smoothened signal transduction pathway (Incardona J. P. et al. (1998) Development 125:3553-3562; Cooper M. K. et al. (1998) Science 280:1603-1607). The sonic hedgehog protein, a member of the hedgehog family of proteins, has been found to induce differentiation of its target cells, including the precursors of ventral cells in the developing central nervous system (Goodrich L. V. et al. (1998) Neuron 21:1243-1257). Inhibition of the hedgehog/smoothened pathway by cyclopamine in the developing chicken brain prevented formation of the ventral cells and caused holoprosencephaly (Incardona J. P. et al. (1998) Development 125:3553-3562; Cooper M. K. et al. (1998) Science 280: 1603-1607), the common malformation observed in the lambs of the sheep grazing Veratrum (Binns W. et al. (1963) Am. J. Vet. Res. 24:11641175). Cyclopamine has been reported to inhibit cellular differentiation in other systems as well, including the differentiation of bone marrow cells to erythroid cells (Detmer K. et al. (2000) Dev. Biol. 222:242) and the differentiation of the urogenital sinus to prostate (Berman D. M. et al. (2000) J. Urol. 163:204).

SUMMARY OF THE INVENTION

This invention concerns the use of cyclopamine, a naturally occurring steroidal alkaloid known for over thirty years, for the treatment of psoriasis and achievement of rapid clearance of the psoriatic skin lesions together with the reversion of the histopathological signs of disease to normalcy with no detectable side effects. The cyclopamine-induced clearance of psoriatic lesions from the skin of patients is associated with the causation of cellular differentiation in lesional epidermis and with the rapid disappearance of CD4(+) lymphocytes and other inflammatory cells from lesional skin. Therapeutic compositions comprising of cyclopamine and a corticosteroid and/or the pre-treatment of lesions with a corticosteroid provide significantly further increased therapeutic effectiveness over the use of cyclopamine alone or a corticosteroid alone (the latter displays insignificant or marginal effectiveness when used for less than a week).

According to one aspect, the present invention is directed to the use of cyclopamine or a pharmaceutically acceptable salt or a derivative thereof for clearing CD4 positive lymphocytes from psoriatic lesions in human patients.

In a second aspect, the invention is directed to the use of cyclopamine or a pharmaceutically acceptable salt or a derivative thereof for causation of the differentiation of the epidermal cells in psoriatic lesions in human patients.

In a further aspect, the invention is directed to the use of cyclopamine or a pharmaceutically acceptable salt or a derivative thereof for restoring the decreased or lost cytokeratin 15 expression in the epidermal basal layer of psoriatic lesional skin in human patients, and/or the use of cyclopamine or a pharmaceutically acceptable salt or a derivative thereof for attaining decrease or disappearance of erythema from psoriatic lesional skin in human patients within 12 hours of application.

Preferably, regression and clearance of psoriatic lesions are obtained within 1-8 days, without harming the non-lesional skin. With therapeutic compositions comprising of cyclopamine or a pharmaceutically acceptable salt or derivative thereof and a corticosteroid and/or pretreatment of lesions with a corticosteroid, regression and clearance of psoriatic lesions are obtained within 1-4 days, commonly within 1-2 days. Most preferably, treatment for a day with therapeutic compositions comprising of cyclopamine or a pharmaceutically acceptable salt or a derivative thereof and a cortiscosteroid provides regression and clearance of psoriatic lesions.

BRIEF DESCRIPTION OF THE FIGURES

The application file of the parent application Ser. No. 10/682,662, filed Oct. 9, 2003, which has been incorporated by reference herein in its entirety, contains at least one drawing executed in color.

Figures

FIG. 2A shows a section from the non-lesional skin tissue. Hematoxylene-Eosine (H&E) staining, 200× original magnification.

FIG. 2W shows a tissue section from the junctional area of the cyclopamine-treated and non-treated lesional skin at the 24th hour, stained immunohistochemically with the MT310 antibody. 40× original magnification. Disappearance of the CD4 positive lymphocytes from the dermis of treated area (towards the left of figure) are seen.

Figures

FIG. 3A shows non-lesional skin tissue of a patient with psoriasis. H&E, 200× original magnification.

FIG. 3B shows a tissue section from the non-treated psoriatic lesional skin of the same patient as in FIG. 3A. H&E, 200× original magnification.

FIG. 3C shows a tissue section from the cyclopamine-treated psoriatic lesion of the same patient as in FIG. 3A at the 24th hour of treatment. H&E, 200× original magnification.

FIG. 3D shows immunohistochemical staining for the Ki-67 antigen of a non-lesional skin tissue section from a patient with psoriasis vulgaris. 400× original magnification.

FIG. 3E shows immunohistochemical staining for the Ki-67 antigen of a tissue section from a non-treated psoriatic lesion of the same patient as in FIG. 3D. 400× original magnification. Numerous Ki-67 displaying cell are seen in the suprabasal layers in epidermis.

FIG. 3F shows immunohistochemical staining for the Ki-67 antigen of a tissue section from a cyclopamine-treated psoriatic lesion of the same patient as in FIG. 3D at the 24th hour of treatment. 400× original magnification. Return of the Ki-67 displaying cells to the epidermal basal layer is seen.

FIG. 3G shows non-lesional skin tissue of a patient with psoriasis stained immunohistochemically for the epithelial antigen using the Ber-EP4 antibody. 100× original magnification.

FIG. 3H shows a tissue section from a non-treated psoriatic lesional skin of the same patient as in FIG. 3G stained immunohistochemically for the epithelial antigen using the Ber-EP4 antibody. 100× original magnification.

FIG. 3I shows a tissue section from a cyclopamine-treated psoriatic lesion of the same patient as in FIG. 3G at the 24th hour of treatment, stained immunohistochemically for the epithelial antigen using the Ber-EP4 antibody. 100× original magnification.

FIG. 3J shows non-lesional skin tissue of a patient with psoriasis stained immunohistochemically with the C8/144B antibody that binds the human CD8 antigen and the cytokeratin 15. 100× original magnification.

FIG. 3K shows a tissue section from a non-treated psoriatic plaque of the same patient as in FIG. 3J stained immunohistochemically with the C8/144B antibody that binds the human CD8 antigen and the cytokeratin 15. 200× original magnification.

FIG. 3L shows a tissue section from a cyclopamine-treated psoriatic lesion of the same patient as in FIG. 3J at the 24th hour of treatment stained immunohistochemically with the C8/144B antibody that binds the human CD8 antigen and the cytokeratin 15. 200× original magnification.

DESCRIPTION OF THE INVENTION

Figure 1A:
FIG. 1A shows appearance of a psoriatic lesion (about 11×13 mm) at the dorsum of hand of a 57-year old man prior to the application of treatment.

This invention relates to the use of cyclopamine, a naturally occurring steroidal alkaloid known for over thirty years, for the treatment of psoriasis and the achievement of rapid clearance of psoriatic lesions from the patient skin as fast as within a day with no detectable side effects. Disappearances of the clinical signs of psoriasis, including the erythema and scaling, from the skin of patients are accompanied by the reversions of the histopathological signs of psoriasis to normalcy and are achievable by topical treatment. Follow-up of the treated skin areas shows healthy-looking normal skin over months. These features make the use of cyclopamine highly desirable in the treatment of psoriasis and provide a solution to the long-standing problem of psoriasis treatment. Therapeutic compositions comprising of cyclopamine or a pharmaceutically acceptable salt or a derivative thereof and a corticosteroid and/or the pretreatment of lesions with a corticosteroid provide significantly further increased therapeutic effectiveness over the use of either alone.

For topical applications, cyclopamine can be dissolved in ethanol or another suitable solvent and mixed with a suitable base cream, ointment or gel or a foam preparation. Cyclopamine may also be entrapped in hydrogels or in other pharmaceutical forms enabling controlled release and may be adsorbed onto dermal patches. In a pharmaceutical preparation for topical administration, the cyclopamine or a pharmaceutically acceptable salt or derivative thereof should be present in a concentration of 0.001 mM to 100 mM, preferably in a concentration of 9 mM to 24 mM. The effects shown in figures FIG. 1A to FIG. 1F (clinical pictures) and FIG. 2A to FIG. 2W and FIG. 3A to FIG. 3L (histopathological and immunohistochemical findings) have been obtained by a cream preparation obtained by mixing a solution of cyclopamine in ethanol with a base cream so as to get a final concentration of 18 mM cyclopamine in cream. The base cream used is made predominantly of heavy paraffin oil (10% w/w), vaseline (10% w/w), stearyl alcohol (8% w/w), polyoxylsteareth-40 (3% w/w) and water (68% w/w) but another suitably formulated base cream is also possible. Optimal concentration of cyclopamine in a pharmaceutical form as well as the optimal dosing and application schedules can obviously be affected by such factors as the particular pharmaceutical form and the localization and characteristics of the skin lesion; however these can be determined by following well known published optimization methods. The dosing and the application schedules followed for the lesion shown in FIG. 1A (psoriatic plaque on the dorsum of hand) are as follows: about 30 µl cream applied directly onto the lesion with the aid of a steel spatula every four hours for 24 hours. The cream-applied area is protected from accidental smearing and loss of the cream by covering with an aluminum applicator (FIG. 1B). The dosing and the application schedules followed for the lesion shown in FIG. 1D (psoriatic plaque at the scapular region) are as follows: about 30 µl cream applied directly onto the lesion every four hours for 24 hours. The cream-applied area is similarly covered against the smearing and loss of cream. Other treated psoriatic patients and lesions received from about 30 to 35 µl cream to each lesion at intervals of every 3 to 5 hours, as suitable and convenient. Lesions were similarly covered against the smearing and loss of cream. Placebo cream (the base cream mixed with ethanol with no added cyclopamine) applications onto comparably sized psoriatic plaques as the cyclopamine-treated psoriatic plaques followed the same dosing, schedule and covering of the lesions; placebo-treated psoriatic plaques showed no detectable effect or regression (data not shown). Preservation of the undifferentiated cells in the normal epidermis and in hair follicles following exposure to cyclopamine, as described in an earlier patent application by us (Taş S. et al. (2001) PCT/TR 01/00027) as well as in this invention, provide information about the tolerable doses in other possible modes of administration of cyclopamine; e.g. intralesional injections or covering with suitable dermal patches and timed-release formulations or systemic administration of aqueous solutions or of cyclopamine entrapped in liposomes. In preparing therapeutic compositions comprising of cyclopamine and a corticosteroid, mixing of the two in the same pharmaceutical carrier is facilitated by their similar molecular structures (both being steroidal molecules) and by their similar lipid versus water solubility characteristics. Optimal concentrations of cyclopamine and a corticosteroid in a pharmaceutical form can obviously be affected by such factors as the particular pharmaceutical form and the particular corticosteroid and the mode of administration; however, these can be determined by following well known published methods of optimization. The therapeutic effect shown in FIG. 4D was obtained by a cream preparation comprising of about 9 mM cyclopamine and about 0.55 mM clobetasol 17-propionate in base cream made predominantly of heavy paraffin oil (10% w/w), vaseline (10% w/w), stearyl alcohol (8% w/w), polyoxylsteareth-40 (3% w/w) and water (68% w/w). The corticosteroid used for treatment of the lesion shown in FIG. 4E was clobetasol 17-propionate in a final concentration of about 1.1 mM in base cream. Similar corticosteroid actions are obtained by substituting the clobetasol 17-propionate in this cream with about 50 mM hydrocortisone. In a pharmaceutical preparation comprising of cyclopamine or a pharmaceutically acceptable salt or derivative thereof and a corticosteroid, cyclopamine or a pharmaceutically acceptable salt or derivative thereof should exist in a concentration of 0.001 mM to 100 mM, preferably in a concentration of 9 mM to 24 mM, and clobetasol 17-propionate should be present in a concentration of 0.2 mM to 1.5 mM. Other corticosteroid molecules well known in the art are contemplated to be also suitable and capable of replacing the above-mentioned corticosteroid molecules at suitable concentrations (the suitable concentration ranges for corticosteroids are also known in the art).

The unprecedented therapeutic effectiveness of the treatment described herein is based on highly reproducible biological effects associated with the specific molecular and cellular changes that are also described herein. It is therefore specifically contemplated that other molecules can be derived from cyclopamine or synthesized in such a way that they exert similar receptor-binding properties and biological and therapeutic effects as cyclopamine. Such molecules are called here as derivatives of cyclopamine. The term derivatives of cyclopamine, as used here, is defined as follows:

A molecule that contains the region of cyclopamine molecule involved in the binding of cyclopamine to its biological target but contains in addition modifications of the parent cyclopamine molecule in such ways that the newly derived molecule continues to be able to bind specifically to the same biological target (i.e. the smoothened protein) to exert the biological effects of cyclopamine disclosed in this invention. Such modifications of cyclopamine may include one or more permissible replacement of or deletion of a molecular group in the cyclopamine molecule or addition of a molecular group (particularly a small molecular group such as the methyl group) to the cyclopamine molecule provided that the resultant molecule is stable and possesses the capability of specific binding to the same biological target as cyclopamine to exert the biological effects of cyclopamine disclosed in this invention. Derivation of such new molecules from cyclopamine can be readily achieved by those skilled in the art and the continuance or abolishment of the possession of the biological effects of cyclopamine in the newly derived molecule can also be readily determined by those skilled in the art, for example by testing for the biological effects disclosed in this application.

Figure 1B:
FIG. 1B shows the same lesion as in FIG. 1 A with the cyclopamine cream applied to its proximal half (upper in the figure) and covered against accidental smearing and loss.
Figure 1C:
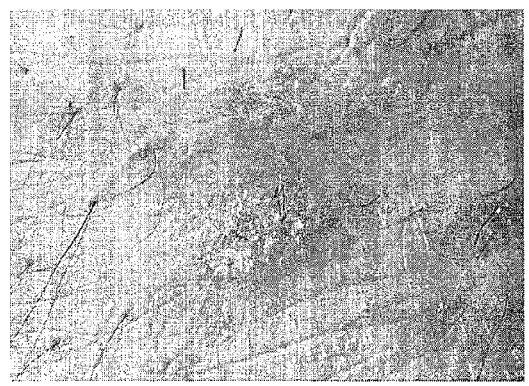
FIG. 1C shows the same lesion as in FIG. 1A at the 24th hour of exposure to the cyclopamine cream. Regression of the psoriatic plaque from the cyclopamine—treated proximal half (upper in the figure) is evident.
Figure 1D:
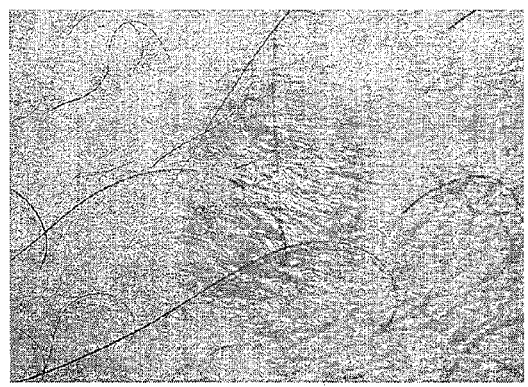
FIG. 1D shows appearance of a psoriatic lesion (about 7×9 mm) at the left scapular region of a 54 year old man prior to the application of cyclopamine.
Figure 1E:
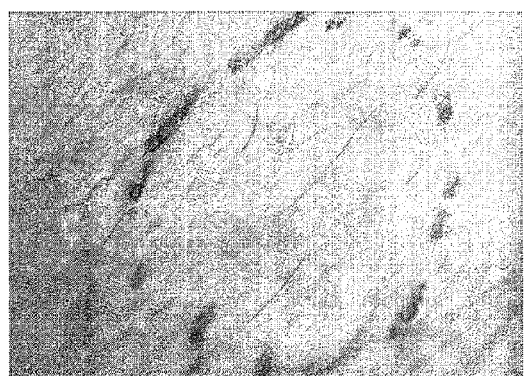
FIG. 1E shows the same skin area as in FIG. 1A after 1 day of treatment and 7 days of follow-up. With the possible exception of slight erythema, lesion is no longer visible.
Figure 1F:
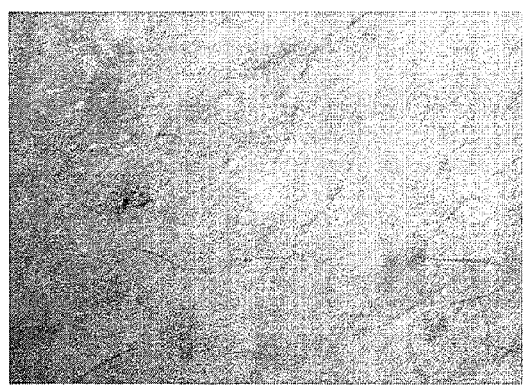
FIG. 1F shows the same skin area as in FIG. 1 E on the 14th day of follow-up. No lesion is visible, skin appears normal.

FIG. 1A and FIG. 1C show a psoriatic plaque before and after exposure to cyclopamine and the rapid clinical regression. The cyclopamine cream was applied to the proximal half of this lesion present on the dorsum of right hand of a 57 years old patient having plaque-type psoriasis. At intervals of 4 hours, approximately 30 µl cream was applied directly onto the lesion and the cream-applied region was covered against accidental smearing and loss of the cream (FIG. 1B). Already on the 4th hour of treatment, the cream-applied half of the psoriatic plaque displayed slight decrease in erythema. The erythema was no longer visible in the cyclopamine-applied half of the lesion at the 12th hour and on the 24th hour, when the erythema and scaling had visibly disappeared from the cyclopamine-treated half (FIG. 1C), the skin area corresponding to the entire former lesion (both the treated and non-treated halves) was excised together with an approximately 5 mm margin of surrounding non-involved skin.

Figure 2A:
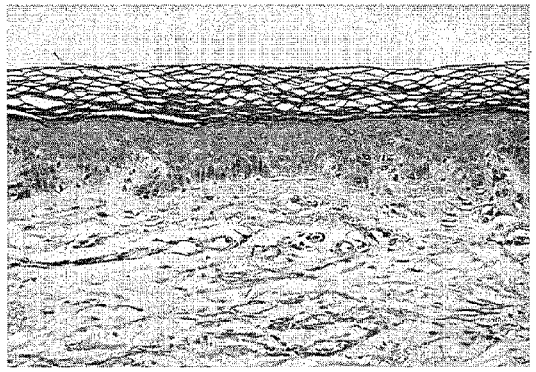
FIG. 2A to FIG. 2W show skin tissue sections from the non-lesional skin, the non-treated psoriatic lesional skin and the cyclopamine-treated lesional skin of the patient presented in Figures FIG. 1A to FIG. 1C.
Figure 2B:
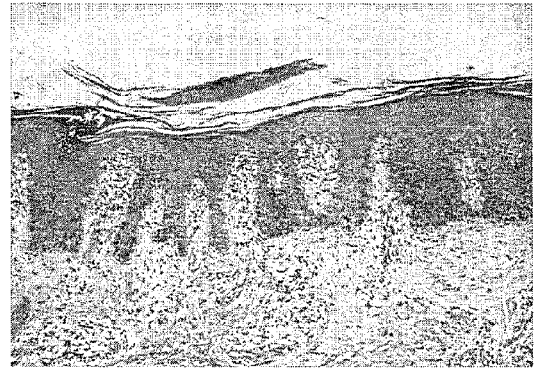
FIG. 2B shows a tissue section from the non-treated psoriatic lesional skin. H&E, 100× original magnification.
Figure 2C:
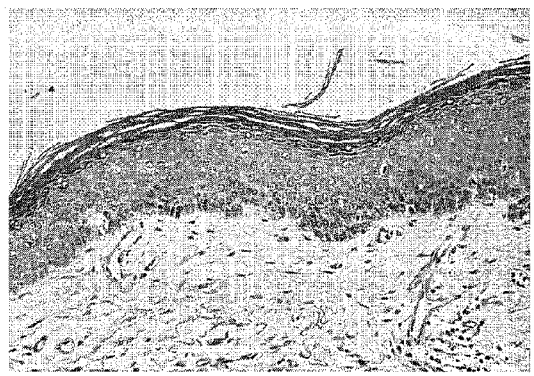
FIG. 2C shows a tissue section from the cyclopamine-treated half of the psoriatic lesion at the 24th hour. H&E, 200× original magnification.
Figure 2D:
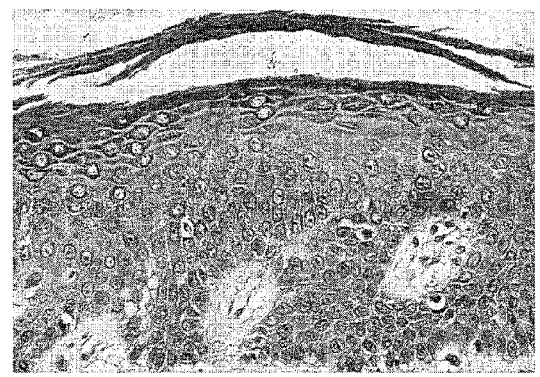
FIG. 2D shows another region from the cyclopamine-treated half of the psoriatic lesion at the 24th hour at 400× original magnification (H&E).
Figure 2E:
FIG. 2E shows a tissue section from the cyclopamine-treated and non-treated junctional area of the psoriatic lesion at the 24th hour. H&E, 200× original magnification.
Figure 2F:
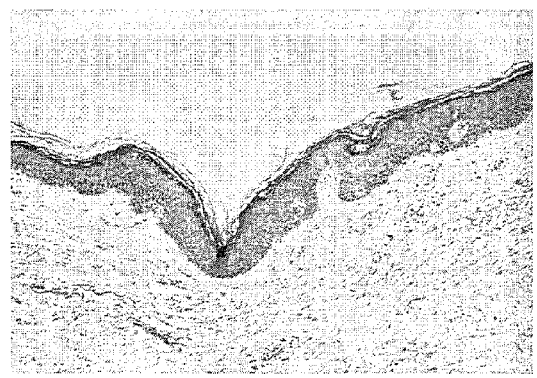
FIG. 2F shows another tissue section from the cyclopamine-treated and non-treated junctional area of the psoriatic lesion at the 24th hour at 100× original magnification (H&E). The area of the psoriatic lesion covered under the applicator with the cyclopamine cream is towards the left of figure (left of the indentation).
Figure 2G:
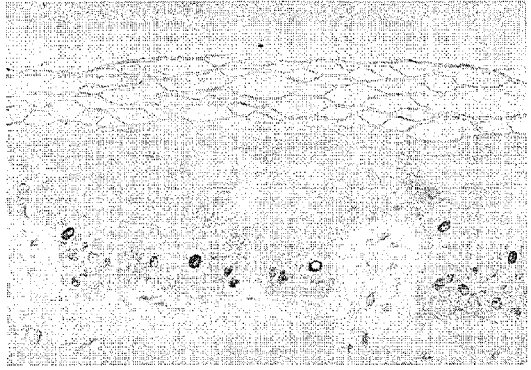
FIG. 2G shows non-lesional skin tissue with immunohistochemically detected Ki-67 antigen. 400× original magnification. Ki-67 displaying cells in the epidermis are seen to be restricted to the basal layer.
Figure 2H:
FIG. 2H shows non-treated psoriatic lesional skin tissue with immunohistochemically detected Ki-67 antigen. 200× original magnification. Numerous Ki-67 displaying cells are seen in the suprabasal layers of epidermis.
Figure 2I:
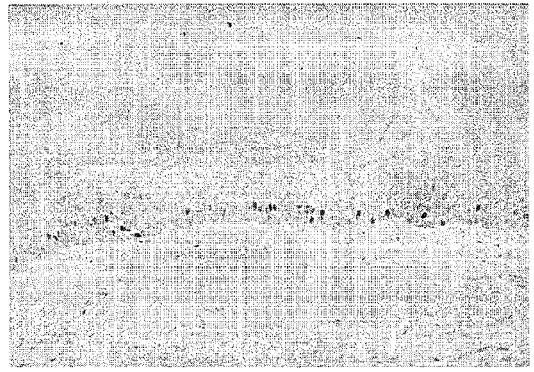
FIG. 2I shows a tissue section from the cyclopamine-treated half of the psoriatic lesion at the 24th hour with immunohistochemical staining for the Ki-67 antigen. 200× original magnification. Return of the Ki-67 displaying cells to the epidermal basal layer is seen.
Figure 2J:
FIG. 2J shows a tissue section from the cyclopamine-treated and non-treated junctional area of the psoriatic lesion at the 24th hour with immunohistochemical staining for the Ki-67 antigen. 200× original magnification. The cyclopamine-receiving tissue is towards the left of figure.
Figure 2K:
FIG. 2K shows a Ki-67 stained tissue section from the junctional area of the non-lesional skin with the cyclopamine-treated half of the psoriatic lesion at the 24th hour. 100× original magnification. The non-lesional skin is towards the left of figure.
Figure 2L:
FIG. 2L shows non-lesional skin tissue stained immunohistochemically for the epithelial antigen by the Ber-EP4 antibody. 100× original magnification. Epidermal basal layer cells are seen to display the epithelial antigen.
Figure 2M:
FIG. 2M shows non-treated psoriatic lesional skin tissue stained immunohistochemically for the epithelial antigen using the Ber-EP4 antibody. 100× original magnification. The Ber-EP4 detectable epithelial antigen is seen to be greatly decreased to non-existent in the psoriatic lesional epidermis.
Figure 2N:
FIG. 2N shows a tissue section from the cyclopamine-treated half of the psoriatic lesion at the 24th hour, stained immunohistochemically for the epithelial antigen using the Ber-EP4 antibody. 400× original magnification. Epidermal basal layer cells are seen to display the epithelial antigen.
Figure 2O:
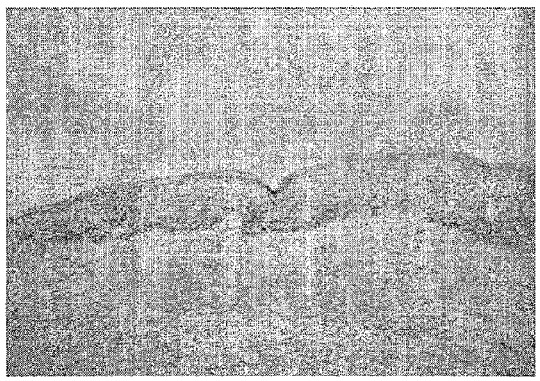
FIG. 2O shows a tissue section from the cyclopamine-treated and non-treated junctional area of the psoriatic lesion at the 24th hour, stained immunohistochemically for the epithelial antigen by the Ber-EP4 antibody. 100× original magnification. The area of the psoriatic lesion covered under the applicator with the cyclopamine cream is towards the left of figure (left of the indentation).
Figure 2P:
FIG. 2P shows a tissue section from the junctional area of the non-lesional skin with the cyclopamine-treated half of the psoriatic lesion at the 24th hour. Immunohistochemical staining for the epithelial antigen using the Ber-EP4 antibody is shown at 100× original magnification. Non-lesional skin is towards the left of figure.
Figure 2R:
FIG. 2R shows non-lesional skin tissue stained immunohistochemically with the C8/144B antibody that binds the human CD8 antigen and the cytokeratin 15. 400× original magnification.
Figure 2S:
FIG. 2S shows a tissue section from the junctional area of the non-lesional skin with the non-treated lesional skin. Immunohistochemical staining with the C8/144B antibody shown at 100× original magnification. Non-lesional skin is towards the left of figure.
Figure 2T:
FIG. 2T shows a tissue section from the cyclopamine-treated half of the psoriatic lesion at the 24 h hour, stained immunohistochemically using the C8/144B antibody. 400× original magnification.
Figure 2U:
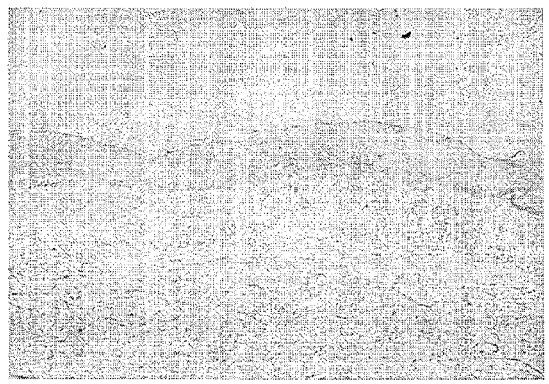
FIG. 2U shows a tissue section from the junctional area of the non-lesional skin with the cyclopamine-treated lesional skin at the 24th hour, stained immunohistochemically using the C8/144B antibody. 100× original magnification. Non-lesional skin is towards the left of figure.
Figure 2V:
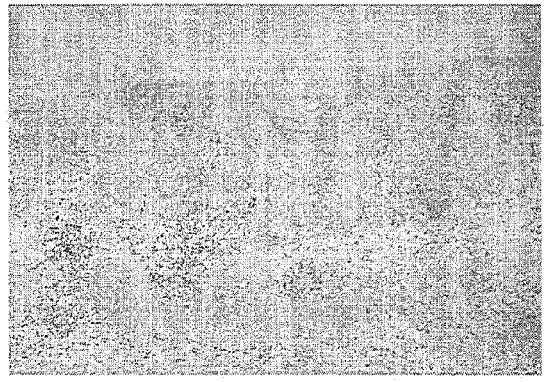
FIG. 2V shows a tissue section from the non-treated psoriatic lesional skin stained immunohistochemically With the MT310 antibody that binds the human CD4 antigen. 100× original magnification. Abundant CD4 positive lymphocytes are seen to infiltrate the dermis.
Figure 2W:
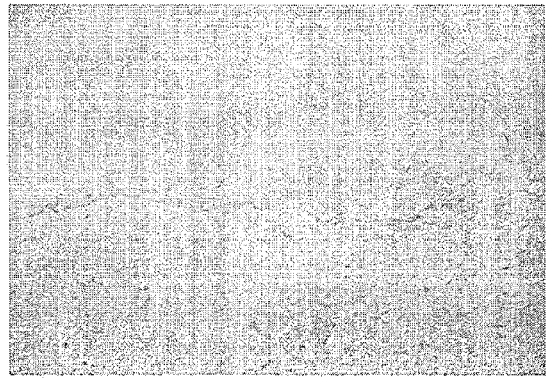

Figures FIG. 2A to FIG. 2W show histopathological and immunohistochemical examination findings of the tissue sections from the non-lesional skin, cyclopamine-treated lesional skin and non-treated lesional skin. Compared to the non-lesional skin (FIG. 2A), the non-treated lesional skin (FIG. 2B) is seen to display the typical histopathological signs of a psoriatic skin lesion mentioned above in the "Background of Invention". Tissue sections from the cyclopamine-treated half of the original lesion reveal, however, dramatic improvement and regression to normalcy. These histopathological signs of regression to normalcy, exemplified in the figures FIG. 2C and FIG. 2D (examples from other cyclopamine-treated lesions and patients are given later) include the following:

Return of the thickened and elongated rete ridges to normal levels and marked decrease of epidermal hyperplasia (FIG. 2C versus FIG. 2B).

Return of the thinning of the suprapapillary epidermis to normalcy and the disappearance of papillary edema (FIG. 2C versus FIG. 2B).

Vigorous re-appearance of the granular layer of epidermis in the cyclopamine-treated epidermis (FIG. 2C and FIG. 2D) contrasted with the focally decreased or lost granular layer in the non-treated lesional epidermis (FIG. 2B).

Disappearance from the cyclopamine-treated lesional skin of most of the inflammatory cells that infiltrated the subepidermal dermis of the non-treated lesional skin (FIG. 2C versus FIG. 2B).

The hyperkeratosis and parakeratosis seen in the stratum corneum of the non-treated lesional skin (FIG. 2B) decreased but full normalization of this oldest epidermal layer did not yet happen at the 24th hour of cyclopamine treatment (FIG. 2C, FIG. 2D). Tissue sections from the junctional area of the cyclopamine-treated and non-treated lesional skin revealed that regions of the lesional skin that received relatively lesser concentrations of cyclopamine (by diffusion from the nearby treated area) still displayed signs of regression towards normalcy but relatively less pronouncedly (FIG. 2E, FIG. 2F).

Relevant immunohistochemical findings with the tissues described above are summarized below and exemplified through figures FIG. 2G to FIG. 2W. All antibodies and reagents for these immunohistochemical investigations were purchased from DAKO (Glostrup, Denmark); human Ki-67 antigen was detected by the monoclonal antibody M7187, human epithelial antigen was detected by the monoclonal antibody Ber-EP4, human CD4 antigen was detected by the monoclonal antibody M0716, human CD8 antigen was detected by the monoclonal antibody C8/144B. Besides the CD8 antigen, the monoclonal antibody C8/144B is known to recognize and bind to the cytokeratin 15 expressed by the hair stem cells (Kanitakis J. et al. (1999) Eur. J. Dermatol. 9:363-365). A DAKO universal visualization kit (LSAB2) employing biotinylated secondary antibody and peroxidase-conjugated streptavidin (pre-diluted to match the dilutions of DAKO-supplied primary antibodies) was used for the visualization reactions. All reaction conditions were as recommended by the manufacturer.

The Ki-67 antigen is a marker of the proliferating cells. As shown in FIG. 2G, the Ki67 displaying cells were restricted mostly to the basal layer in the epidermis of non-lesional skin. Sections of the non-treated lesional skin showed, on the other hand, increased numbers of Ki-67 positive cells in the epidermis and numerous Ki-67 positive cells in the suprabasal layers of epidermis (FIG. 2H), as is well known for psoriasis. FIG. 2I shows return of both the frequency and the epidermal position of the Ki-67 antigen positive cells to normalcy in cyclopamine-treated lesional skin. Tissue sections of the junctional areas of the cyclopamine-treated lesional skin with the non-treated lesional skin (FIG. 2J) and with the non-lesional skin (FIG. 2K) show again the normalizing effect of cyclopamine on the frequency and epidermal position of Ki-67 positive cells and provide evidence of a concentration-dependent effect of cyclopamine.

The monoclonal antibody Ber-EP4 is known to label the basal layer cells in normal epidermis. The outer root sheath of hair follicles, where the hair stem cells are thought to reside, are also known to be labeled with Ber-EP4. FIG. 2L shows that non-lesional skin showed a normal pattern of labeling with Ber-EP4 (i.e. labeling of the basal layer cells). The non-treated psoriatic lesional epidermis, on the other hand, showed absence of labeling of the basal layer with Ber-EP4 under the same conditions (FIG. 2M). This Ber-EP4 detected abnormality of the basal layer cells in the psoriatic lesional epidermis, as far as we know previously undescribed, reverted to normalcy upon treatment of the lesion with cyclopamine (FIG. 2N).

FIG. 2O shows a Ber-EP4 stained tissue section from the cyclopamine-treated and non-treated junctional area of the psoriatic lesion. The normalizing action of cyclopamine on the psoriatic lesion at a distance suggests sensitivity of the Ber-EP4 detected abnormality to cyclopamine. Exposure of the basal cell carcinoma cells to cyclopamine was found earlier to cause their differentiation and caused loss of their Ber-EP4 staining (Taş S. et al. (2001) PCT/TR 01/00027). Basal cells of the normal epidermis exposed to cyclopamine under the same conditions, however, continued to be Ber-EP4 positive (Taş S. et al. (2001) PCT/TR 01/00027). FIG. 2P shows that basal cells of the non-lesional skin in psoriasis also remained Ber-EP4 positive after exposure to cyclopamine; the basal cell characteristics were maintained.

Cytokeratin 15, recognized by the C8/114B antibody, is found normally both in the hair follicle and in the basal layer cells in normal epidermis (Kanitakis J. et al (1999) Eur. J. Dermatol. 9:363-365). FIG. 2R shows the labeling of the basal layer cells by C8/144B in non-lesional skin. In contrast, basal layer cells of the non-treated psoriatic lesional skin were stained very weakly or not at all with the C8/144B antibody (FIG. 2S). On the other hand, epidermal basal layer cells in the cyclopamine-treated half of the lesional skin were normalized and became labeled by the C8/144B antibody (FIG. 2T). As both C8/144B and Ber-EP4 detect both the outer root sheath cells and the normal epidermal basal layer cells, the basal cell abnormality revealed by these two antibodies in the psoriatic lesional epidermis may be related or identical. Cyclopamine did not adversely affect the non-lesional skin and, similar to the situation with Ber-EP4, basal cells of the non-lesional epidermis that Were exposed to cyclopamine continued to be positive for the cytokeratin 15 (FIG. 2U).

Infiltration of dermis with CD4 positive lymphocytes, a well-known feature of psoriatic plagues, was displayed by the non-treated psoriatic lesional skin (FIG. 2V). On the other hand, the CD4 positive lymphocyles infiltrating the psoriatic lesional skin were largely cleared from the cyclopamine-treated half of the lesional skin (FIG. 2W). Clearance of the CD4 positive lymphocytes from psoriatic lesional skin rapidly following application of cyclopamine thereto is highly surprising, since termination of the hedgehog/smoothened signalling was shown in the prior art to be necessary for the conversion of CD4-CD8 double negative T lymphocytes to the CD4-CD8 double positive T lymphocytes [Outram S V et al (2000) *Immunity* 13; 187-197]. Specifically, formation of CD4-CD8 double positive lymphocytes from CD4-CD8 double negative lymphocytes was shown to be enhanced by cyclopamine [Outram S V et al (2000) *Immunity* 13:187-197]. Moreover, conversion of the CD4(−) and CD8(−) lymphocytes to the CD4 (+) and CD8(+) lymphocytes is viewed widely in the prior art as a requirement for their psoriatic plaque causing action [reviewed in Krueger J G (2002) *Journal of the American Academy of Dermatology* 46:1-23].

Genetic heterogeneity and different ages of the psoriatic patients as well as the localizational heterogeneity of psoriatic lesions throughout body invite evaluation of the use of cyclopamine on different patients and lesions. In this invention, treatments of unrelated patients ranging from 29 years of age to 57 years and treatments of psoriatic lesions localized on various body parts ranging from extremities to the trunk showed that cyclopamine was highly effective on every psoriatic lesion for which it was used and resulted in regression and clearance (7 separate lesions on different patients were treated at the time of writing of this invention) [with additional psoriatic patients and lesions treated since the filing of PCT/TR 02/00017, the number of separate lesions that have been treated exceeds 25 (summarized below)]. Figures FIG. 1 D, FIG. 1 E and FIG. 1 F show that even when cyclopamine was applied for a day and then discontinued, the psoriatic plaque that received the treatment continued to regress and cleared totally. In this particular case the psoriatic plaque displayed decreased erythema on the 12th hour of treatment. Despite marked regression, it Was still visible on the fourth day of follow-up. The lesion cleared after day 8 and the site of the treated lesion is displaying healthy-looking normal skin over a month of follow-up at the time of writing of this invention. Cyclopamine, applied topically on healthy skin as disclosed in this invention and earlier (Ta§ S. et al. (2001) PCT/TR 01/00027) had no detectable adverse effect. The longest duration of follow-up for a possible adverse effect of topical cyclopamine on healthy skin is over 14 months at the time of writing of this invention and no adverse effect has been found (skin sites of cyclopamine application were followed up also in the interval since the filing of PCT/TR 02/00017 and show healthy-looking normal skin and hair over a period of more than 31 months now suggesting functional preservation as well of the stem cells and long-term safety).

Figures FIG. 3C to FIG. 3L show skin tissue sections from the non-lesional skin, non-treated psoriatic lesional skin and the cyclopamine-treated lesional skin of different patients (patients other than the one described in figures FIG. 2A to FIG. 2W) and further exemplify the uses and findings of this invention.

Figure 3A:
FIG. 3A to FIG. 3L show skin tissue sections from the non-lesional skin, the non-treated lesional skin and the cyclopamine-treated lesional skin of various patients (age range 29 years to 57 years and the range of disease duration 1.5 years to 6 years) with psoriasis vulgaris.
Figure 3B:
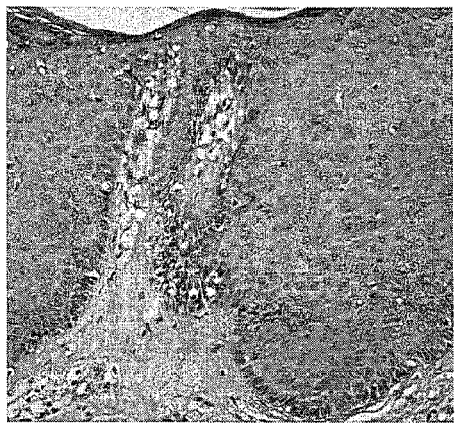
Figure 3C:

Figures FIG. 3A, FIG. 3B and FIG. 3C show histopathological findings with non-lesional skin tissue, non-treated psoriatic lesional skin tissue and cyclopamine-treated psoriatic lesional skin tissue at the 24th hour of treatment and exemplify the cyclopamine-induced regression of the psoriatic plaque on a patient.

Figure 3D:
Figure 3E:
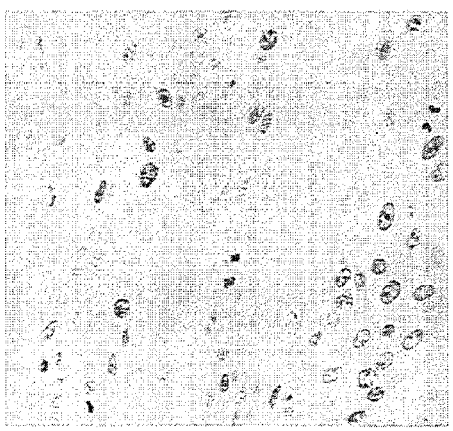
Figure 3F:

Figures FIG. 3D, FIG. 3E and FIG. 3F show immunohistochemical staining for the Ki-67 antigen of non-lesional skin tissue, non-treated psoriatic lesional skin tissue and cyclopamine-treated lesional skin tissue at the 24th hour of treatment and exemplify the cyclopamine-induced regression of another psoriatic plaque.

Figure 3G:
Figure 3H:
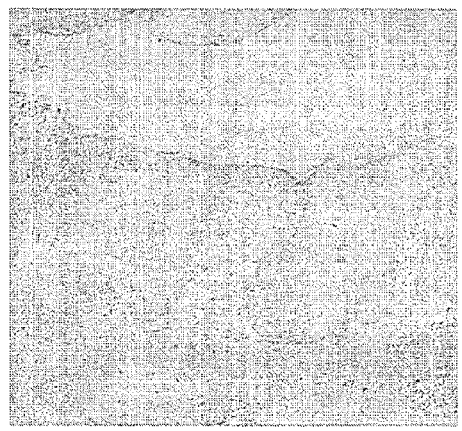
Figure 3I:
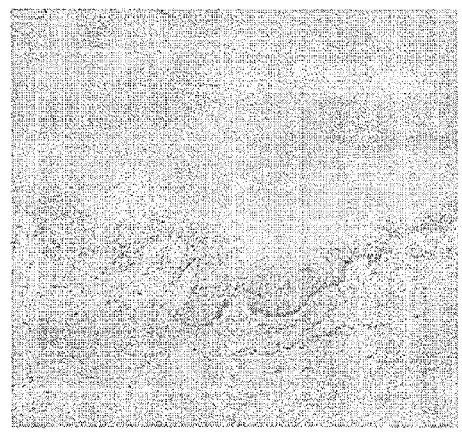

Figures FIG. 3G, FIG. 3H and FIG. 3I show immunohistochemical staining using the Ber-EP4 antibody of the non-lesional skin tissue, non-treated psoriatic lesional skin tissue and cyclopamine-treated psoriatic lesional skin tissue at the 24th hour of treatment and exemplify on another patient the Ber-EP4 detected abnormality of the basal layer cells in the psoriatic lesional skin as well as the cyclopamine-induced reversion to normalcy.

Figure 3J:
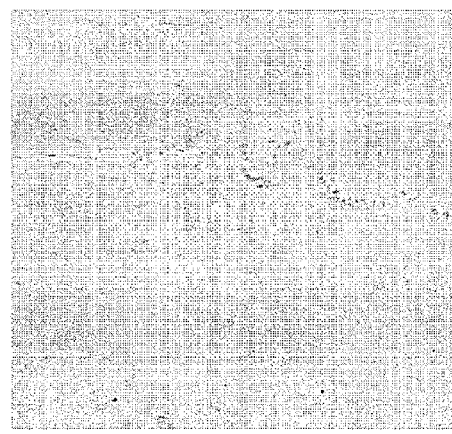
Figure 3K:
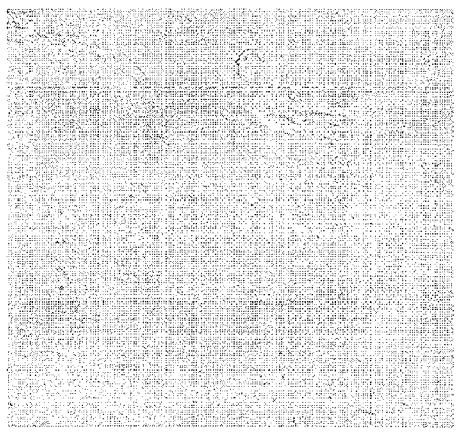
Figure 3L:
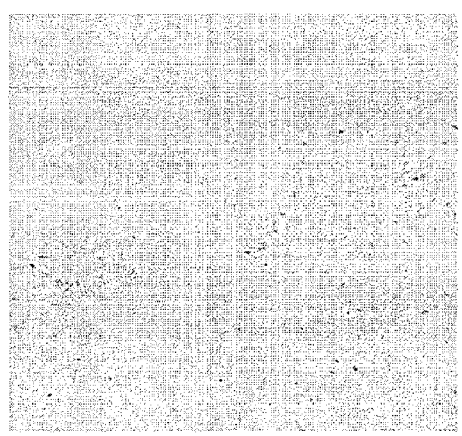

Figures FIG. 3J, FIG. 3K and FIG. 3L show immunohistochemical staining with the C8/144B antibody of the non-lesional skin tissue, non-treated psoriatic lesional skin tissue and cyclopamine-treated psoriatic lesional skin tissue at the 24th hour of treatment and exemplify on a different patient the C8/144B detected abnormality of the basal layer cells in the psoriatic lesional skin as well as the cyclopamine-induced reversion to normalcy. Cytokeratin 15 that is bound by the C8/144B antibody [Kanitakis J. et al. (1999) *European Journal of Dermatology* 9:363-365] has been known as a protein expressed in the basal layer of epidermis and in the bulge region of the outer root sheath of hair follicles where the follicle/epidermis stem cells are thought to reside [Lyle S. et al. (1998) *Journal of Cell Science* 111:3179-3188]. As hedgehog/smoothened signaling is required for the maintenance of epithelial stem cells [Zhang Y. et al. (2001) *Nature* 410:599-604], consistent restoration of the lost cytokeratin 15 expression to the epidermal basal layer of psoriatic lesional skin following exposure to cyclopamine is surprising.

Figure 4A:
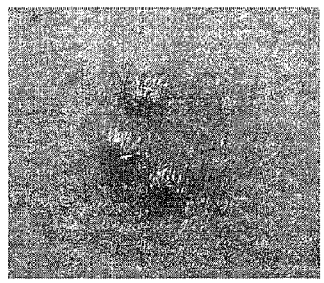
FIG. 4A shows appearance of a psoriatic lesion (approximately 7×8 mm) in the antecubital region of a 29-year old man prior to treatment.
Figure 4B:
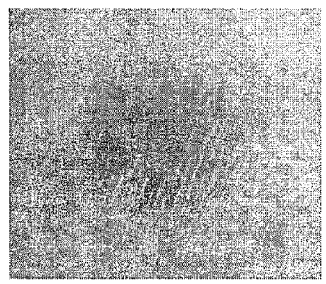
FIG. 4B shows the same lesion as in FIG. 4B after treatment with the cyclopamine cream for 24 hours and follow-up without treatment for 44 hours (68th hour from the onset of treatment).

FIG. 4A shows a psoriatic plaque on the antecubital region of a 29-year old man prior to treatment. Approximately 20 µl of the cyclopamine cream (18 mM cyclopamine in the base cream described above) was applied onto this lesion every fourth hour for 24 hours. Treatment was then discontinued and the lesion was followed-up. The lesion showed decrease of erythema on the eighth hour of treatment and then continued regression also during the non-treated follow-up to reach to the state shown in FIG. 4B on day three and became undetectable on day four.

Figure 4C:
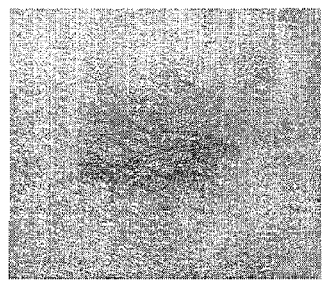
FIG. 4C shows a psoriatic lesion (approximately 9×11 mm) in the deltoid region of a 29-year old man prior to treatment.
Figure 4D:
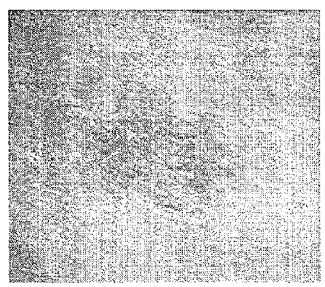
FIG. 4D shows the same lesion as in FIG. 4C on the 68th hour of treatment with a pre-mixed cream containing equal volumes of the cyclopamine cream and a cream preparation of clobetasol 17-propionate (0.5 mg/g).
Figure 4E:
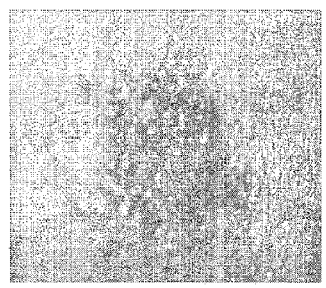
FIG. 4E shows a psoriatic lesion (approximately 11×12 mm) in the hypochondrial region of a 29-year old man after 48 hours of treatment with a cream preparation of clobetasol 17-propionate (0.5 mg/g).
Figure 4F:
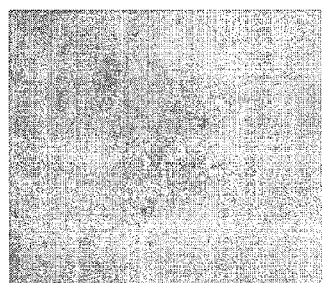
FIG. 4F shows the same lesion as in FIG. 4E on the 24th hour of switching the treatment from clobetasol 17-propionate (0.5 mg/g) to the cyclopamine cream.

FIG. 4C shows another psoriatic plaque located on the deltoid region skin of the same patient prior to treatment. Approximately 20 µl of a cream preparation containing about 9 mM cyclopamine and about 0.55 mM clobetasol-17 propionate (in base cream) was applied onto this lesion every fourth hour. This lesion also displayed decrease of erythema on the eighth hour and became undetectable on day three (FIG. 4 D shows its appearance on the 68th hour). In the same patient other psoriatic lesions that were covered with a cream preparation containing about 1.1 mM clobetasol-17-propionate (but no cyclopamine) on every fourth or eight hour showed no detectable change during the same period (i.e. the lesions were persisting on day three). The enhanced therapeutic response to cyclopamine, even at half of the concentration we were using on other lesions of the same patient, prompted further evaluation of the therapeutic compositions comprising of cyclopamine and a corticosteroid. We evaluated in addition pretreatment of the psoriatic lesions with a topical corticosteroid followed by treatment with the cyclopamine cream (18 mM cyclopamine in base cream). FIG. 4E shows a psoriatic plaque on the hypochondrial region of the same patient prior to the applications of cyclopamine. This lesion was treated with the corticosteroid cream alone for 48 hours, corticosteroid was then discontinued and the treatment was switched to the applications of about 20 µl cyclopamine cream (18 mM cyclopamine in base cream) every fourth hour. FIG. 4F shows the lesion on the 24th hour of the cyclopamine cream applications and shows near complete disappearance of the lesion within only a day.

Severity of psoriatic lesions can be assessed on a semi-quantitative scale by giving separate scores for the erythema, elevation and scaling of a lesion and then by summing up the scores to obtain a score called the EES score of that lesion (Bowman P. H. et al. (2002) *J. Am. Acad. Dermatol.* 46:907-913). Table I shows comparisons of the therapeutic responses to various forms of treatment, evaluated by the EES scoring. It is seen that use of a therapeutic composition comprising of cyclopamine and a corticosteroid in the treatment of psoriatic lesions enhanced therapeutic effectiveness significantly in comparison to the use of a composition containing only cyclopamine in base cream. Pre-treatment of lesions with corticosteroid for a day, followed by treatment with the cyclopamine cream (18 mM cyclopamine in base cream), enhanced the therapeutic effectiveness similarly. Treatment of lesions with a topical corticosteroid (clobetasol 17-propionate, about 1.1 mM) alone, on the other hand, was unable to cause a significant regression or clearance of the lesions during the four days of treatment (Table I). Table I shows that psoriatic lesions treated for a day regressed but in general at a relatively slower pace in comparison to the continued use of cyclopamine (i.e. in comparison to the application every fourth hour of a therapeutic composition containing cyclopamine until the lesion cleared, usually within about 3-4 days). In the treatments for a single day, once again, a therapeutic composition comprising of cyclopamine and a corticosteroid or pre-treatment of lesion for a day with corticosteroid proved to be more effective than the use of cyclopamine alone (Table I). While the possibility of therapeutic effectiveness with a single day of treatment may be attractive to some patients, most patients are likely to prefer the faster clearance of lesions attained with the continued use of medication. Furthermore, some lesions, subjected to the single-day treatment (about 29%, all in the group treated with cyclopamine alone and none in the group treated with a composition comprising of cyclopamine and corticosteroid) failed to clear completely and exhibited even increase of the EES score around the end of 1st week (data not shown). Thus, uninterrupted use of a therapeutic composition comprising of cyclopamine and a corticosteroid offers to patients at present the fastest and most effective clearance of psoriatic lesions (Table I). The mechanism behind this synergistic action is not clear at present. However, lack of effectiveness of a corticosteroid alone during the approximately 2 to 4 days of treatment that suffices for the lesion-clearing action of a composition comprising of cyclopamine and a corticosteroid is consistent with the intervention by cyclopamine (but not by corticosteroids) with (a) key/proximal pathogenic event(s).

Figure 4G:
FIG. 4G shows a tissue section from the junctional area of non-treated psoriatic lesional skin (to the left of figure) and the adjacent non-lesional skin (to the right of figure) with immunohistochemical staining for the CD44 antigen. Expression of CD44, which increases normally with the differentiation of epidermal keratinocytes, is seen to be significantly decreased in the suprabasal and spinous cells of psoriatic lesional skin in comparison to the situation in non-lesional epidermis. 5× original magnification.
Figure 4H:
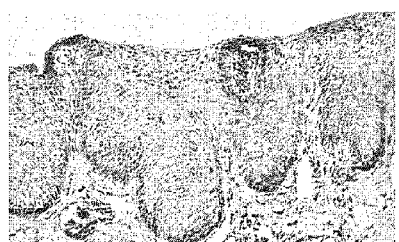
FIG. 4H shows higher magnification (200×) view of a section from the non-treated psoriatic lesional skin with immunohistochemical staining for the CD44 antigen. Expression of CD44 in the suprabasal and spinous layers is seen to be decreased in comparison to the situation in non-lesional epidermis.
Figure 4I:
FIG. 4I shows a tissue section from the lesional skin with immunohistochemical staining for the CD44 antigen on the 24th hours of treatment with cyclopamine. 200× original magnification. Notice the increase and normalization of the expression of CD44 following treatment with cyclopamine (compare to the non-treated lesional skin in FIG. 4H) as well as the near normalization of epidermal hyperplasia.

What might be the key/proximal pathogenic event(s) intervened by cyclopamine? While not wishing to be bound to any theory, we note the differentiation-inducing activity of cyclopamine as important in this regard. Studies published prior to this invention reported a blocking of the cellular differentiation by cyclopamine and suggested that cyclopamine may be used for preventing differentiation (Detmer K. et al (2000) *Dev. Biol.* 222:242; Berman D. M. et al. (2000) *J. Urol.* 153:240). However, we have found that the exposure of psoriatic lesional skin to cyclopamine induced rather differentiation of the epidermal cells. Re-appearance of the granular layer in the epidermis of the cyclopamine-treated psoriatic lesional skin shows that the block to differentiation in the psoriatic plaque was overcome by the cyclopamine treatment. Other findings shown in FIGS. 4G, 4H and 4J also show rapid induction of the differentiation of epidermal cells in the psoriatic lesional skin in response to the treatment with cyclopamine. Expression of the cell adhesion molecule CD44 is known to increase normally with the differentiation of epidermal basal cells to the upper layer spinous cells [Kooy A. J. et al (1999) *Human Pathology* 30:1328-1335] FIG. 4G shows a tissue section from the junctional area of non-treated psoriatic lesional skin (to the left of figure) and adjacent non-lesional skin (to the right of figure) with immunohistochemical staining for the CD44 antigen (anti-human CD44 antibody F10-44-2 binding to the CD44 standard was purchased from Novocastra Labs. Ltd., U.K. and immunohistochemical staining using peroxidase was performed under conditions recommended by the manufacturer). Both FIG. 4G and a closer-up view on FIG. 4H show decreased CD44 expression in the suprabasal and spinous layers in lesional epidermis in comparison to the situation in non-lesional epidermis. FIG. 4I, showing a tissue section from the lesional skin on the 24th hour of treatment with cyclopamine, shows rapid induction and normalization of the CD44 expression following treatment.

Figure 4J:
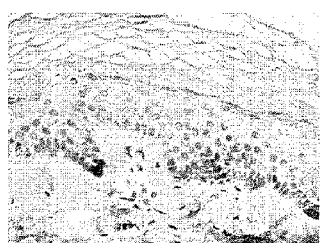
FIG. 4J shows non-lesional skin tissue with immunohistochemically detected EGFR. The EGFR displaying cells in the epidermis are seen to be restricted to the basal layer. 200× original magnification.
Figure 4K:
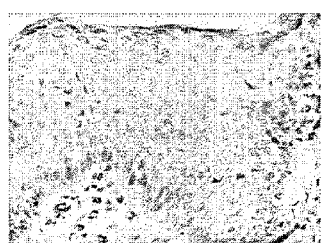
FIG. 4K shows non-treated psoriatic lesional skin tissue with immunohistochemically detected EGFR. Suprabasal cells in the lesional epidermis are seen to show markedly increased EGFR expression. 200× original magnification.
Figure 4L:
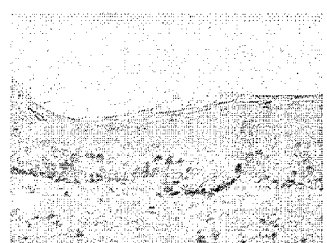
FIG. 4L shows psoriatic lesional skin tissue that was treated with the cyclopamine cream for 24 hours before excision and then stained immunohistochemically for EGFR. The EGFR displaying cells in the epidermis are seen to be restricted to the basal layer. 200× original magnification.

Epidermal growth factor receptor (EGFR) is another marker known to display downregulation of expression with the differentiation of epidermal keratinocytes. Expressions of both EGFR and one or more of its ligands are known to be markedly increased in psoriatic lesional epidermis and may set an autocrine stimulation loop. Ordinarily EGFR expression is not detected immunohistochemically in the suprabasal layers of normal epidermis and the return of EGFR expression to the basal layer of epidermis is regarded to be one of the first signs of effective treatment of psoriasis by various modalities [King LE Jr. et al (1990) *Journal of Investigative Dermatology* 95:105-125]. We evaluated the EGFR expression with anti-human EGFR antibody EGFR 113 (Novocastra Lab. Ltd., U.K.) and With immunohistochemical staining with peroxidase. FIG. 4J shows normal pattern of expression of the EGFR in non-lesional epidermis. Both placebo-treated and non-treated psoriatic lesional skin displayed marked overexpression of the EGFR in the suprabasal layers of epidermis (FIG. 4K). FIG. 4L shows that the EGFR expression was rapidly normalized within 24 hours of the treatment of psoriatic lesional skin with cyclopamine. Thus, treatment of psoriatic lesional skin with cyclopamine was accompanied with the rapid induction of differentiation and therapeutic effect by the criterion of EGFR expression.

We disclose that besides in psoriasis, cyclopamine is effective in inducing differentiation of epidermal cells also in other skin diseases having a unifying feature of being associated with the inhibition of cellular differentiation. The treatment we describe can therefore provide good therapeutic effectiveness on those diseases associated with impairment of cellular differentiation.

Above-summarized immunohistochemical findings as well as the re-appearance of granular layer in the epidermis of cyclopamine-treated psoriatic lesional skin point out to the rapid overcoming of the differentiation block of epidermal cells following the described treatment. While not wishing to be bound by any particular theory, the finding of this invention on the Ki-67 antigen expression by the epidermal cells in the cyclopamine-treated psoriatic lesional skin may also be related to an induction of differentiation by cyclopamine. Disappearance of proliferating cells from the suprabasal layers of the psoriatic lesional epidermis following exposure to cyclopamine (FIG. 2H versus FIG. 2I and FIG. 3E versus FIG. 3F) may be consequential to a regain of the potential for terminal differentiation. In this regard, it should also be noted that a highly potent inhibitor of cellular proliferation, methotrexate, has for many years been used in the treatment of psoriasis but display much lesser (and delayed) therapeutic effectiveness than the treatment described herein. Nevertheless, regardless of the precise mechanism, return of the over-proliferative activity of the psoriatic lesional epidermis to normal levels following exposure to cyclopamine is by itself beneficial (has therapeutic value).

Rapid clearance of the psoriatic plaques as described in this invention (as fast as within a day can be contrasted with the average of 6 to 8 weeks of treatment required for the conventional treatments to become effective (Al-Suwaidan S. N. et al. (2000) J. Am. Acad. Dermatol. 42:796-802; Lebwohl M. et al. (2001) J. Am. Acad. Dermatol. 45:649-661). Thus, the treatment described in this invention represents a major improvement and solution to a long-standing problem. The rapidity of the response to cyclopamine suggests in addition intervention with a proximal causative event involved in the formation of the psoriatic plaque.

As there is evidence for the involvement of the hedgehog/smoothened signal transduction pathway in the maintenance of epidermal stem cells, untoward side effects of cyclopamine on skin are, a priori, possible and must be excluded. As described in this invention and earlier (Taş S. et al. (2001) PCT/TR 01/00027), under the described concentration and dosing conditions no adverse effect has been detected. Lack of detectable side effects of the described treatment combined with hitherto unachieved high topical effectivity represents a solution to the therapeutic dilemma that aggressive uses of conventional treatments often result in unacceptable adverse effects but their less aggressive uses may leave the patient with his/her lesions of psoriasis (Al-Suwaidan S. N. et al (2000) J. Am. Acad. Dermatol. 42:796-802).

TABLE I

Semi-quantitative Evaluation Of The Responses Of Psoriatic Lesions To Different Types Of Treatment

| Treatment | ESS score* of the psoriatic lesions before and on days 2 and 4 of treatment (mean ± S.D.) | | |
|---|---|---|---|
| | Pre-Treatment | Day 2 | Day 4 |
| Base Cream | 6.6 ± 1.0 | 6.2 ± 0.6 | 6.0 ± 0.6 |
| CS Cream | 6.8 ± 0.6 | 6.4 ± 0.8 | 6.5 ± 0.8 |
| Cyclopamine Cream | 6.6 ± 0.4 | 1.4 ± 1.0 | 0.6 ± 0.5 |
| (Cyclopamine + CS) Cream | 6.7 ± 0.9 | 0.5 ± 0 | 0 ± 0 |
| Cyclopamine Cream, 1 day | 6.8 ± 1.6 | 1.8 ± 0.6 | 1.1 ± 0.5 |
| (Cyclopamine + CS) Cream, 1 day | 6.7 ± 1.3 | 1.1 ± 0.4 | 0.4 ± 0.3 |

*Sum of the erythema, elevation and scaling scores (each on a 0 to 4 scale with 0.5 increments). Numbers of lesions scored in each treatment category are 5, 4, 5, 5, 7 and 7 (respectively, in the same order as shown in the Table starting with base cream).
Scores of the lesions that were excised before day 4 for histopathological/immunohistochemical analyses are not included in this evaluation and calculations. "CS Cream" refers to treatment with a cream preparation containing about 1.1 mM clobetasol-17-propionate. "Cyclopamine Cream" refers to treatment with 18 mM cyclopamine in the base cream. "(Cyclopamine + CS) Cream" refers to treatment with a cream preparation containing about 9 mM cyclopamine and about 0.55 mM clobetasol-17-propionate or to treatment with a cream preparation containing 18 mM cyclopamine after a day of pre-treatment with a cream preparation containing about 1.1 mM clobetasol-17-propionate. Results of these two types of treatment were similar and were therefore calculated as a single group. The "1 day" treatments refer to treatments where treatment with a cream containing cyclopamine was continued for one day only. The lesions were then followed up without treatment and the EES scores were determined.

The invention claimed is:

1. A pharmaceutical composition comprising, in combination,
   (i) cyclopamine or another compound that specifically inhibits Hedgehog/Smoothened signaling and
   (ii) a corticosteroid.

2. A pharmaceutical composition according to claim 1, wherein the corticosteroid is clobetasol 17-propionate or hydrocortisone.

3. A pharmaceutical composition according to claim 1, wherein said composition is a pharmaceutical form enabling controlled release.

4. A pharmaceutical composition according to claim 1, wherein said composition is adsorbed onto a dermal patch.

5. A pharmaceutical composition according to claim 1, wherein said composition is in the form of a cream or ointment or gel or hydrogel or foam.

6. A pharmaceutical composition according to claim 1, wherein said composition is entrapped in liposomes or is in the form of an aqueous solution suitable for systemic administration.

7. A pharmaceutical composition according to claim 1 further comprising a pharmaceutically acceptable carrier.

8. A pharmaceutical composition according to any one of claims 1 to 7, wherein said another compound inhibits Hedgehog/Smoothened signaling by binding to the Smoothened protein.

9. A pharmaceutical composition according to any one of claims 1 to 7, wherein said cyclopamine or another compound is cyclopamine or a pharmaceutically acceptable salt thereof.

* * * * *

UNITED STATES PATENT AND TRADEMARK OFFICE
CERTIFICATE OF CORRECTION

PATENT NO. : 7,629,352 B2  
APPLICATION NO. : 11/874653  
DATED : December 8, 2009  
INVENTOR(S) : Sinan Tas It is certified that error appears in the above-identified patent and that said Letters Patent is hereby corrected as shown below:

|  | Change | To |
|---|---|---|
| Column 1, Line 23 | Elder J T at al. | Elder J T et al. |
| Column 1, Line 35 | Well-demarcated | well-demarcated |
| Column 2, Line 53 | 24:11641175 | 24:1164-1175 |
| Column 5, Line 14 | 24 h | 24th |
| Column 5, Line 23 | With | with |
| Column 6, Line 49 | 5x | 50x |
| Column 8, Line 60 and 61 | derivatives of cyclopamine | "derivatives of cyclopamine" |
| Column 11, Line 17 | Were | were |
| Column 13, Line 7 | eight | eighth |

Signed and Sealed this

Fifth Day of October, 2010

David J. Kappos  
*Director of the United States Patent and Trademark Office*